US011123568B2

(12) United States Patent
Moffitt

(10) Patent No.: US 11,123,568 B2
(45) Date of Patent: Sep. 21, 2021

(54) INTERLEAVING STIMULATION PATTERNS PROVIDED BY AN IMPLANTABLE PULSE GENERATOR

(71) Applicant: Boston Scientific Neuromodulation Corporation, Valencia, CA (US)

(72) Inventor: Michael Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 202 days.

(21) Appl. No.: 16/419,853

(22) Filed: May 22, 2019

(65) Prior Publication Data

US 2019/0366107 A1  Dec. 5, 2019

Related U.S. Application Data

(60) Provisional application No. 62/679,430, filed on Jun. 1, 2018.

(51) Int. Cl.
*A61N 1/372* (2006.01)
*A61N 1/05* (2006.01)
*A61N 1/36* (2006.01)

(52) U.S. Cl.
CPC ....... *A61N 1/37247* (2013.01); *A61N 1/0534* (2013.01); *A61N 1/0551* (2013.01);
(Continued)

(58) Field of Classification Search
CPC .............. A61N 1/3724; A61N 1/37252; A61N 1/36189; A61N 1/36185; A61N 1/36164;
(Continued)

(56) References Cited

U.S. PATENT DOCUMENTS 6,181,969 B1  1/2001  Gord
6,516,227 B1  2/2003  Meadows et al.
(Continued)

FOREIGN PATENT DOCUMENTS

| EP | 2209523 A1 | 7/2010 |
|---|---|---|
| WO | 2012/148401 | 11/2012 |
| WO | 2015/095233 | 6/2015 |

OTHER PUBLICATIONS

International Search Report and Written Opinion regarding corresponding PCT Application No. PCT/US2019/033576, dated Jul. 25, 2019.

*Primary Examiner* — Paula J Stice
(74) *Attorney, Agent, or Firm* — Lewis & Reese, PLLC

(57) ABSTRACT

An implantable medical device is configured to receive an input that specifies a time domain allocation between two or more stored stimulation programs and to provide control signals corresponding to each of the two or more stimulation programs to stimulation circuitry to interleave the two or more stimulation programs in time according to the input. The time domain allocation may set a proportion of time during which each of the stimulation programs is active during repeating epochs. The time domain allocation may be set by a user to transition between configured stimulation programs or to specify stimulation that is based on two or more different stimulation programs. The time domain allocation may also be adjusted automatically to optimize an indication of an effectiveness of stimulation that is provided by the patient.

20 Claims, 14 Drawing Sheets

(52) U.S. Cl.
CPC ....... *A61N 1/3603* (2017.08); *A61N 1/36132* (2013.01); *A61N 1/36164* (2013.01); *A61N 1/36175* (2013.01); *A61N 1/36185* (2013.01); *A61N 1/36189* (2013.01); *A61N 1/37252* (2013.01); *A61N 1/37235* (2013.01)

(58) Field of Classification Search
CPC .............. A61N 1/3603; A61N 1/36132; A61N 1/36175; A61N 1/37235; A61N 1/37247; A61N 1/0534; A61N 1/0551; A61N 1/36167; A61N 1/36062
See application file for complete search history.

(56) References Cited

U.S. PATENT DOCUMENTS

| | | |
|---|---|---|
| 7,805,197 B2 | 9/2010 | Bradley |
| 7,890,182 B2 | 2/2011 | Parramon et al. |
| 8,335,569 B2 | 12/2012 | Aghassian |
| 8,498,716 B2 | 7/2013 | Chen et al. |
| 8,560,080 B2 | 10/2013 | Goetz et al. |
| 8,768,453 B2 | 7/2014 | Parramon et al. |
| 9,656,081 B2 | 5/2017 | Feldman et al. |
| 2003/0114899 A1 | 6/2003 | Woods et al. |
| 2004/0210271 A1 | 10/2004 | Campen et al. |
| 2005/0222646 A1 | 10/2005 | Kroll et al. |
| 2008/0177338 A1 | 7/2008 | Ben-David et al. |
| 2009/0083070 A1* | 3/2009 | Giftakis ............. A61N 1/37247 705/2 |
| 2014/0364919 A1* | 12/2014 | Doan ................. A61N 1/36164 607/46 |
| 2015/0080982 A1 | 3/2015 | Funderburk |
| 2018/0071513 A1 | 3/2018 | Weiss et al. |

* cited by examiner

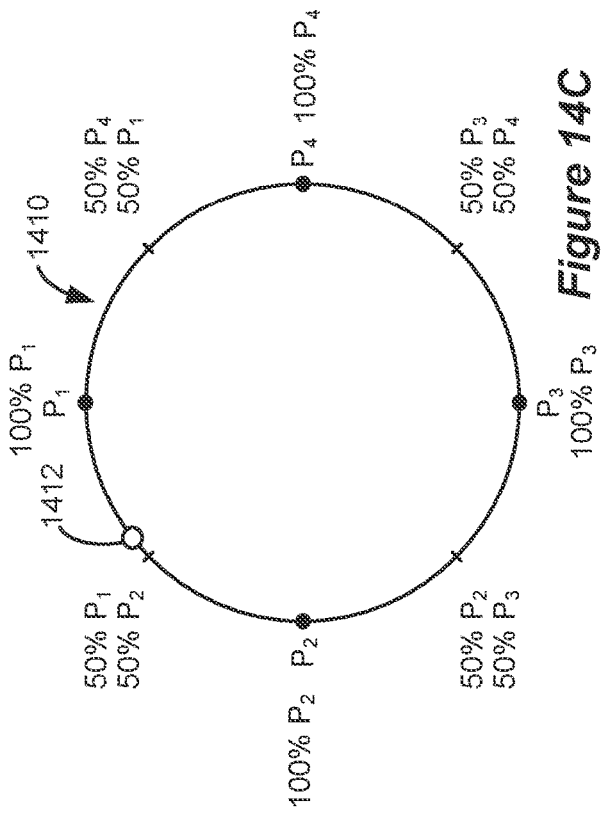
*Figure 14C*
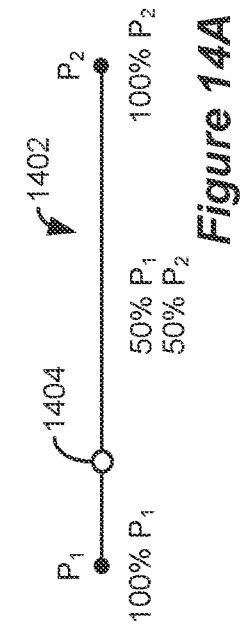
*Figure 14A*
*Figure 14B*
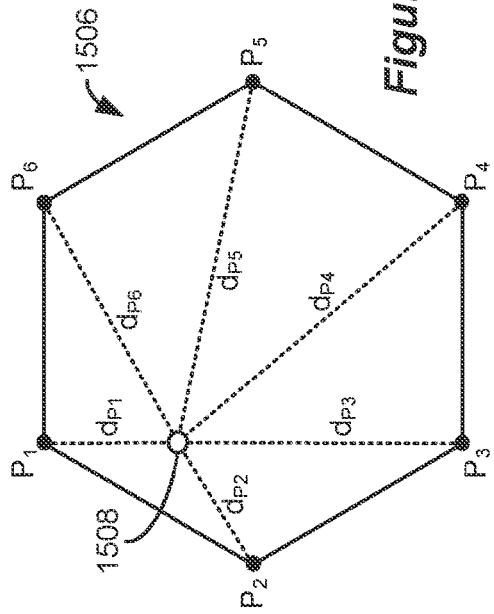
*Figure 15B*
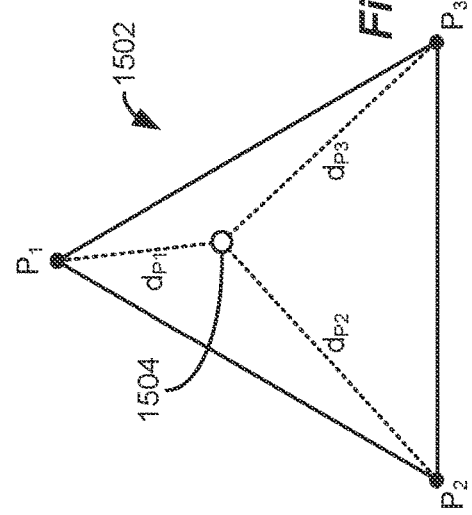
*Figure 15A*

INTERLEAVING STIMULATION PATTERNS PROVIDED BY AN IMPLANTABLE PULSE GENERATOR

CROSS REFERENCE TO RELATED APPLICATIONS

This is a non-provisional application of U.S. Provisional Patent Application Ser. No. 62/679,430, filed Jun. 1, 2018, to which priority is claimed, and which is incorporated by reference in its entirety.

FIELD OF THE TECHNOLOGY

Implantable stimulation devices deliver electrical stimuli to nerves and tissues for the therapy of various biological disorders. The present application is related to a technique to improve the effectiveness of therapy that is provided by implantable stimulation devices.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of a technique in the context of a Spinal Cord Stimulation (SCS) system, such as that disclosed in U.S. Pat. No. 6,516,227. However, the disclosed technique may find applicability in any implantable medical device system, including a Deep Brain Stimulation (DBS) system.

As shown in FIG. 1, a traditional SCS system includes an implantable neurostimulator such as an Implantable Pulse Generator (IPG) 10 (an implantable medical device, more generally), which includes a device case 12 that is formed from a biocompatible material such as titanium. The case 12 typically holds the circuitry and battery 14 (FIG. 2) necessary for the IPG 10 to function, which battery 14 may be either rechargeable or primary in nature. The IPG 10 delivers electrical stimulation to a patient's nerves and tissues through electrodes 16, which, in a SCS system are typically implantable within the epidural space within the patient's spinal column. Common electrode arrangements include a linear arrangement along a percutaneous lead 18 and a two-dimensional arrangement on a paddle lead 60. The proximal ends of the leads 18 and 60 include lead connectors 20 that are connectable to the IPG 10 at one or more connector blocks 22 fixed in a header 24, which can comprise an epoxy, for example. Contacts in the connector blocks 22 make contact with electrode terminals in the lead connectors 20, and communicate with the circuitry inside the case 12 via feedthrough pins 26 passing through a hermetic feedthrough 28 to allow such circuitry to provide stimulation to or monitor the various electrodes 16. The number and arrangement of electrodes 16 on a percutaneous lead 18 or a paddle lead 60 can vary. When percutaneous leads 18 are employed, it is common for multiple such leads 18 to be implanted at different anatomical locations along the spinal canal.

As shown in FIG. 2, IPG 10 contains a charging coil 30 for wireless charging of the IPG's battery 14 using an external charger 50, assuming that battery 14 is a rechargeable battery. If IPG 10 has a non-rechargeable (primary) battery 14, charging coil 30 in the IPG 10 and the external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external devices referenced above, which may be used to communicate with the IPG 10, in plan and cross section views. External controller (or, remote controller) 40 may be used to control and monitor the IPG 10 via a bidirectional wireless communication link 42 that passes through a patient's tissue 5. For example, the external controller 40 may be used to provide or adjust a stimulation program for the IPG 10 to execute. Stimulation programs define a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of fc=125 kHz, with a 129 kHz signal representing transmission of a logic '1' bit and a 121 kHz signal representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing. The functionality of the external controller may alternatively be provided through a software application that is executed on a general purpose device such as a tablet computer or smartphone as opposed to the special purpose device that is shown in FIG. 2.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency ($f_2$=80 kHz) than data communications on link 42. This magnetic field 52 energizes the charging coil 30 in the IPG 10, and the induced voltage is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

SUMMARY

An implantable medical device is disclosed, which may comprise: stimulation circuitry that is configured to provide electrical stimulation to a patient via one or more electrodes that are connectable to the implantable medical device; and control circuitry that is configured to: store stimulation parameters that define a plurality of stimulation programs, wherein each stimulation program defines at least one waveform to be formed at a set of the electrodes; receive an input that specifies a time domain allocation between two or more of the stimulation programs; and provide control signals corresponding to each of the two or more stimulation programs to the stimulation circuitry to interleave the two or more stimulation programs in time according to the input.

The input may further specify a duration of a repeating epoch. The control circuitry may be configured to provide the control signals corresponding to each of the two or more stimulation programs to the stimulation circuitry during a proportion of each epoch according to the time domain allocation.

The input may further specify a time domain allocation mode of operation. The mode of operation may specify that each of the two or more stimulation programs is to be re-initiated during each of its time allocations. The mode of operation may also specify that a position should be stored at an end of each stimulation program's respective time allocation to mark a beginning position in a subsequent time allocation. The mode of operation may still further specify that the two or more stimulation programs are to be continuously running and that the control signals are to be provided to the stimulation circuitry only during each of the two or more stimulation programs' time allocations.

The input may be a user input that is received from an external device. The control signals may be executed by the stimulation circuitry in a single timing channel. Each of the plurality of programs may be independently executable.

An external device is disclosed comprising control circuitry that is configured to: send stimulation parameters that define a plurality of stimulation programs to an implantable medical device, wherein each stimulation program defines at least one waveform to be formed at a set of electrodes that are connectable to the implantable medical device; and send an output that specifies a time domain allocation between two or more of the stimulation programs to the implantable medical device, wherein the output causes the implantable medical device to interleave the two or more stimulation programs in time according to the time domain allocation.

The external device may comprise a display, and the control circuitry may be further configured to present a graphical user interface on the display to enable a user to set the time domain allocation. The graphical user interface may comprise a slider bar that comprises a representation of each of the two or more stimulation programs. The time domain allocation may be set according to the position of a slider relative to the representations. The graphical user interface may comprise a shape that comprises a representation of one of the two or more stimulation programs at each of the shape's vertices. The time domain allocation may be set according to the position of a slider relative to each of the shape's vertices. The graphical user interface may comprise one or more equalizer bars. Each of the equalizer bars may comprise a representation of one of the two or more stimulation programs at each of its ends. Each of the equalizer bars may correspond to a sensory dimension, and wherein the representations at the ends of each equalizer bar represent stimulation programs that provide different sensations for the equalizer bar's sensory dimension. The time domain allocation may be set according to the positions of each slider bar's slider relative to the slider bar's midpoint. Each of the equalizer bars may correspond to one of the two or more stimulation programs.

The control circuitry may be further configured to receive an indication from a patient of an effectiveness of stimulation. The control circuitry may be configured to execute an algorithm to adjust the time domain allocation to optimize the indication of the effectiveness of stimulation.

At least one of the two or more stimulation programs may provide sub-threshold or super-threshold stimulation.

The output may further specify a duration of a repeating epoch. The output may further specify a time domain allocation mode of operation. The mode of operation may specify that each of the two or more stimulation programs is to be re-initiated during each of its time allocations. The mode of operation may specify that a position should be stored at an end of each stimulation program's respective time allocation to mark a beginning position in a subsequent time allocation. The mode of operation may specify that the two or more stimulation programs are to be continuously running and that the control signals are to be provided to the stimulation circuitry only during each of the two or more stimulation programs' time allocations.

The output may specify that the two or more stimulation programs be executed in a single timing channel. Each of the plurality of programs is independently executable by the implantable medical device.

A computer-readable medium is disclosed having instructions stored thereon which may cause control circuitry to: send stimulation parameters that define a plurality of stimulation programs to an implantable medical device, wherein each stimulation program defines at least one waveform to be formed at a set of electrodes that are connectable to the implantable medical device; and send an output that specifies a time domain allocation between two or more of the stimulation programs to the implantable medical device, wherein the output causes the implantable medical device to interleave the two or more stimulation programs in time according to the time domain allocation.

The computer-readable medium may further comprise instructions to cause the control circuitry to present a graphical user interface that enables a user to set the time domain allocation. The graphical user interface may comprise a slider bar that comprises a representation of each of the two or more stimulation programs. The time domain allocation may be set according to the position of a slider relative to the representations. The graphical user interface may comprise a shape that comprises a representation of one of the two or more stimulation programs at each of the shape's vertices. The time domain allocation may be set according to the position of a slider relative to each of the shape's vertices. The graphical user interface comprises one or more equalizer bars. Each of the equalizer bars may comprise a representation of one of the two or more stimulation programs at each of its ends. Each of the equalizer bars may correspond to a sensory dimension, and wherein the representations at the ends of each equalizer bar represent stimulation programs that provide different sensations for the equalizer bar's sensory dimension. The time domain allocation may be set according to the positions of each slider bar's slider relative to the slider bar's midpoint. Each of the equalizer bars may correspond to one of the two or more stimulation programs.

The computer-readable medium may further comprise instructions to cause the control circuitry to receive an indication from a patient of an effectiveness of stimulation. The computer-readable medium may further comprise instructions to cause the control circuitry to execute an algorithm to adjust the time domain allocation to optimize the indication of the effectiveness of stimulation.

At least one of the two or more stimulation programs may provides sub-threshold or super-threshold stimulation.

The output may further specify a duration of a repeating epoch. The output may further specify a time domain allocation mode of operation. The mode of operation may specify that each of the two or more stimulation programs is to be re-initiated during each of its time allocations. The mode of operation may specify that a position should be stored at an end of each stimulation program's respective time allocation to mark a beginning position in a subsequent time allocation. The mode of operation may specify that the two or more stimulation programs are to be continuously running and that the control signals are to be provided to the stimulation circuitry only during each of the two or more stimulation programs' time allocations.

The output may specify that the two or more stimulation programs be executed in a single timing channel. Each of the plurality of programs may be independently executable by the implantable medical device.

BRIEF DESCRIPTION OF THE DRAWINGS

FIGS. 14A-14C illustrate different slider graphical user interfaces for setting the time domain allocation between two stimulation programs in accordance with an example of this disclosure.

FIGS. 15A and 15B illustrate different shape graphical user interfaces for setting the time domain allocation between more than two stimulation programs in accordance with an example of this disclosure.

DETAILED DESCRIPTION

As mentioned above, the electrical stimulation that the IPG 10 is capable of delivering is highly customizable with respect to selected electrodes, electrode current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, it is customary to evaluate the stimulation parameters that might provide effective stimulation therapy for a particular patient using a trial and error approach. Moreover, the stimulation parameters that provide effective therapy for a patient may change over time or in different circumstances. Multiple stimulation programs are therefore typically configured and transmitted and stored on the IPG 10 such that the patient may conveniently select from different pre-configured stimulation programs (e.g., using the controller 40)

Figure 1:
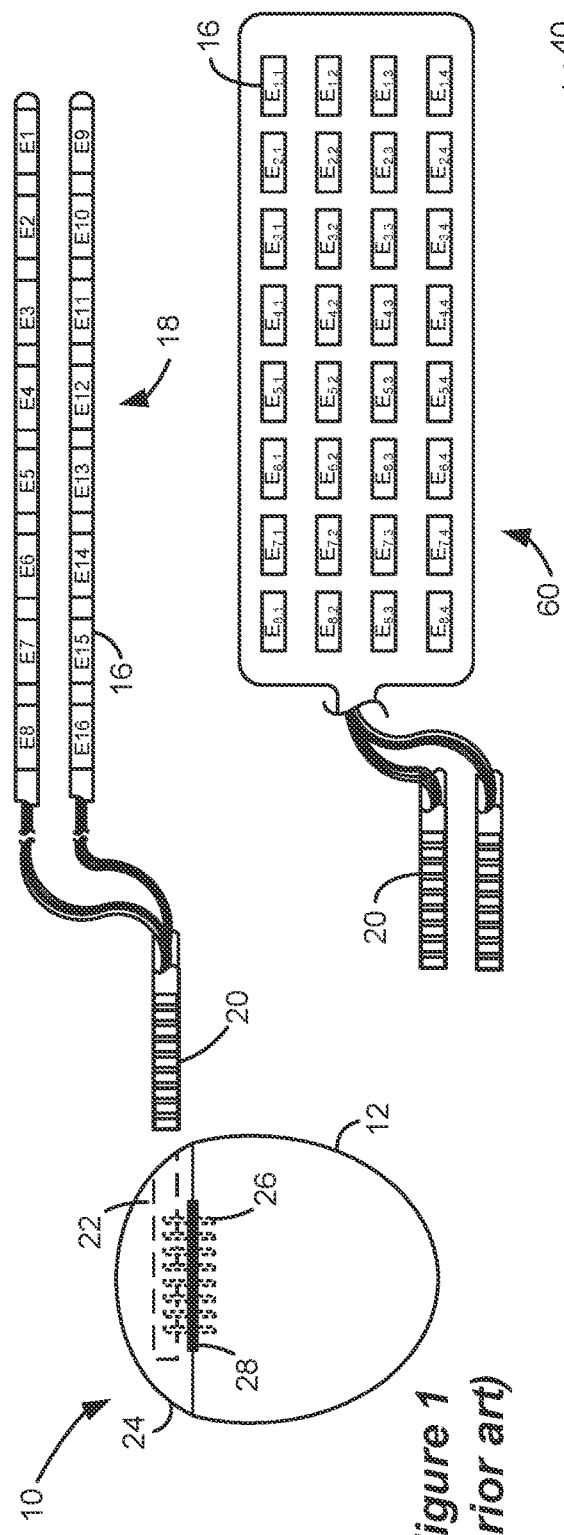
FIG. 1 shows an implantable pulse generator (IPG).
Figure 2:
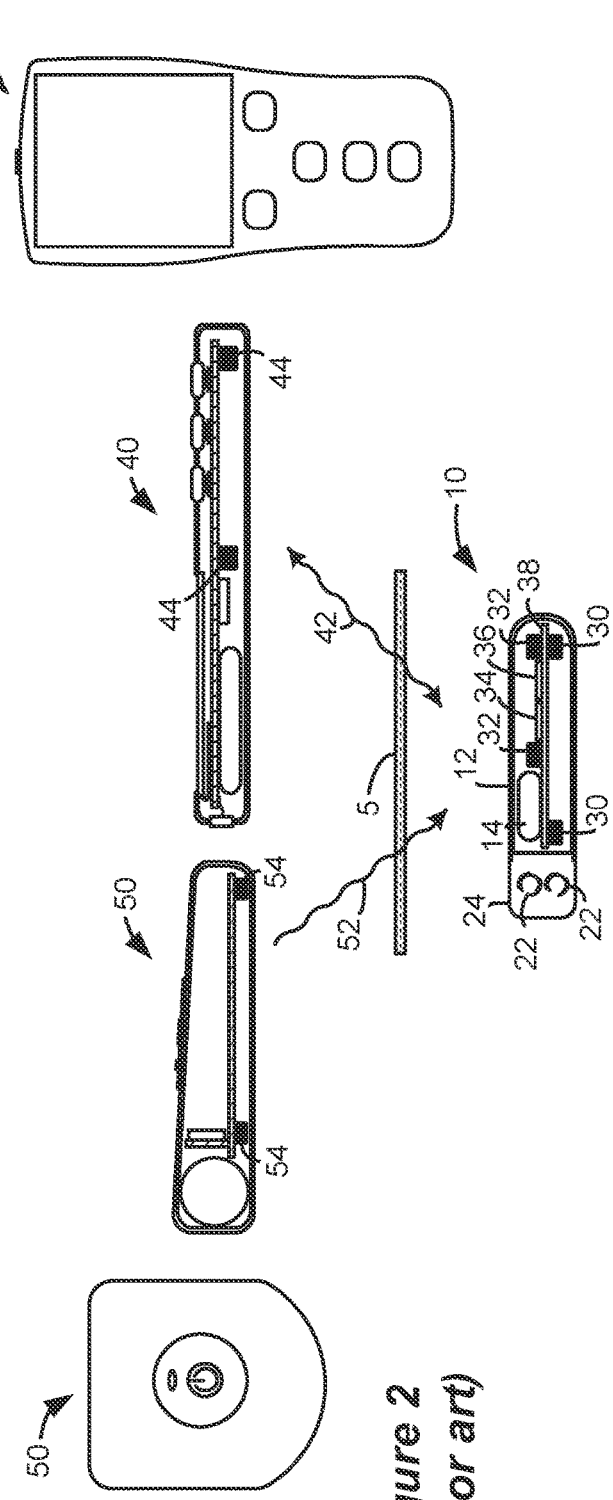
FIG. 2 shows a cross section of the IPG of FIG. 1 as implanted in a patient, as well as external devices that support the IPG, including an external charger and external controller.
Figure 3:
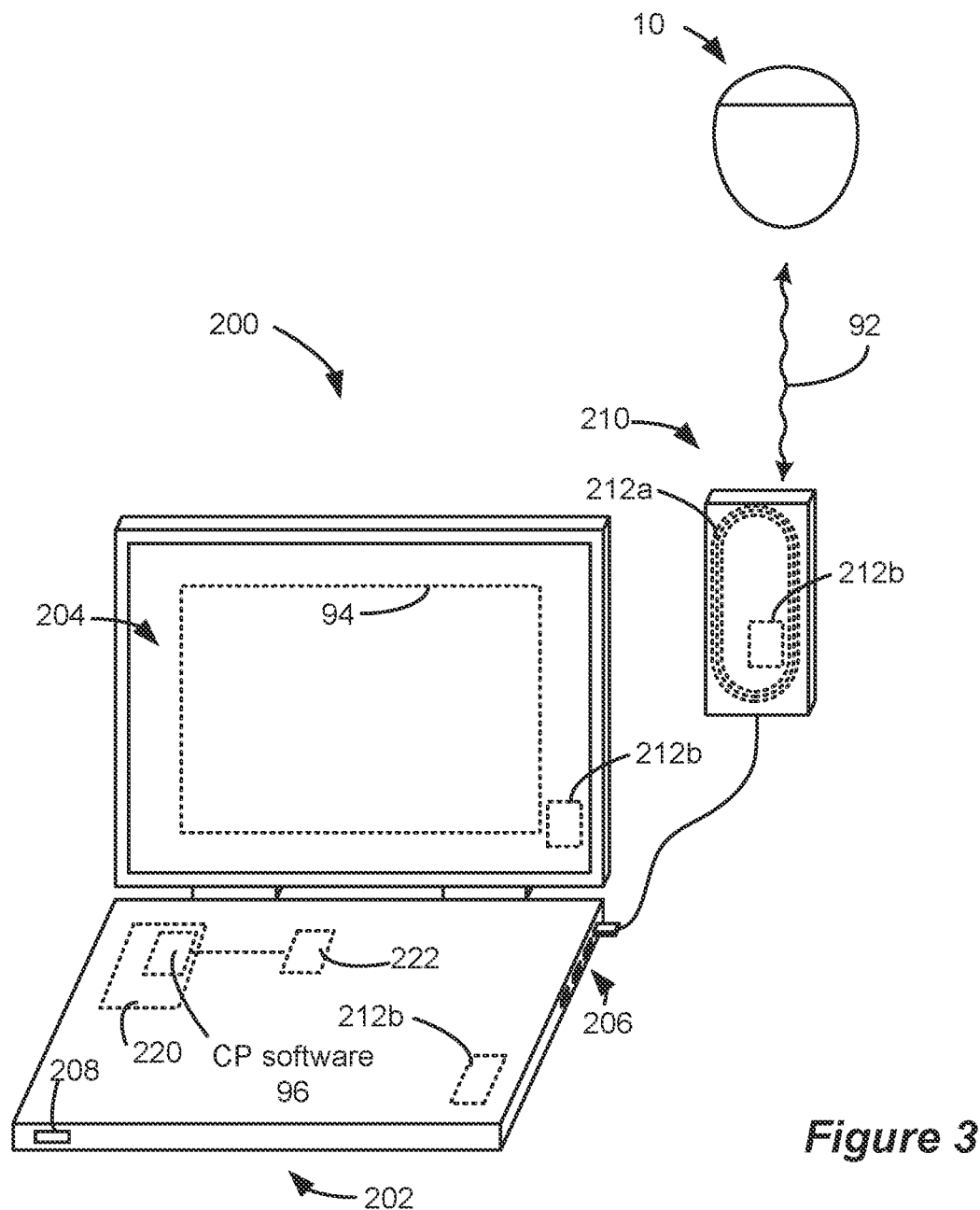
FIG. 3 shows components of a clinician's programmer system, including components for communicating with an IPG in accordance with an example of the disclosure.

The stimulation programs can be configured using and provided via a wired or wireless link (wireless link 92 shown) from an additional external device known as a clinician's programmer 200. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 3, CP computer 202 is shown as a laptop computer that includes typical computer user interface means such as a screen 204, a mouse, a keyboard, speakers, a stylus, a printer, etc., not all of which are shown for convenience. Also shown in FIG. 3 is a communication head 210, which is coupleable to a suitable port on the CP computer 202, such as a USB port 206. While the CP system is shown in communication with the IPG 10 70, the CP system 200 is also configured to communicate with an external trial stimulator that mimics the operation of the IPG 10 during a trial stimulation phase as is known. While the remainder of this disclosure describes the use of disclosed techniques in the context of an IPG 10, the techniques are equally applicable to other neurostimulators such as external trial stimulators.

Communication between the CP system 200 and the IPG 10 may comprise magnetic inductive or short-range RF telemetry schemes as already described, and in this regard the IPG 10 and the CP computer 202 and/or the communication head 210 (which can be placed proximate to the IPG 10) may include antennas compliant with the telemetry means chosen. For example, the communication head 210 can include a coil antenna 212a, a short-range RF antenna 212b, or both. The CP computer 202 may also communicate directly with the IPG 10, for example using an integral short-range RF antenna 212b.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To generate stimulation programs, the clinician interfaces with a clinician's programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer's non-volatile memory 220. Such non-volatile memory 220 may include one or more non-transitory computer-readable storage mediums including, for example, magnetic disks (fixed, floppy, and removable) and tape, optical media such as CD-ROMs and digital versatile discs (DVDs), and semiconductor memory devices such as Electrically Programmable Read-Only Memory (EPROM), Electrically Erasable Programmable Read-Only Memory (EEPROM), and USB or thumb drive. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 enable communications with the ETS 70 or IPG 10 through a suitable antenna 212a or 212b, either in the communication head 210 or the CP computer 202 as explained earlier, so that the clinician can use the CP GUI 94 to communicate the stimulation programs to the IPG 10.

Figure 4:
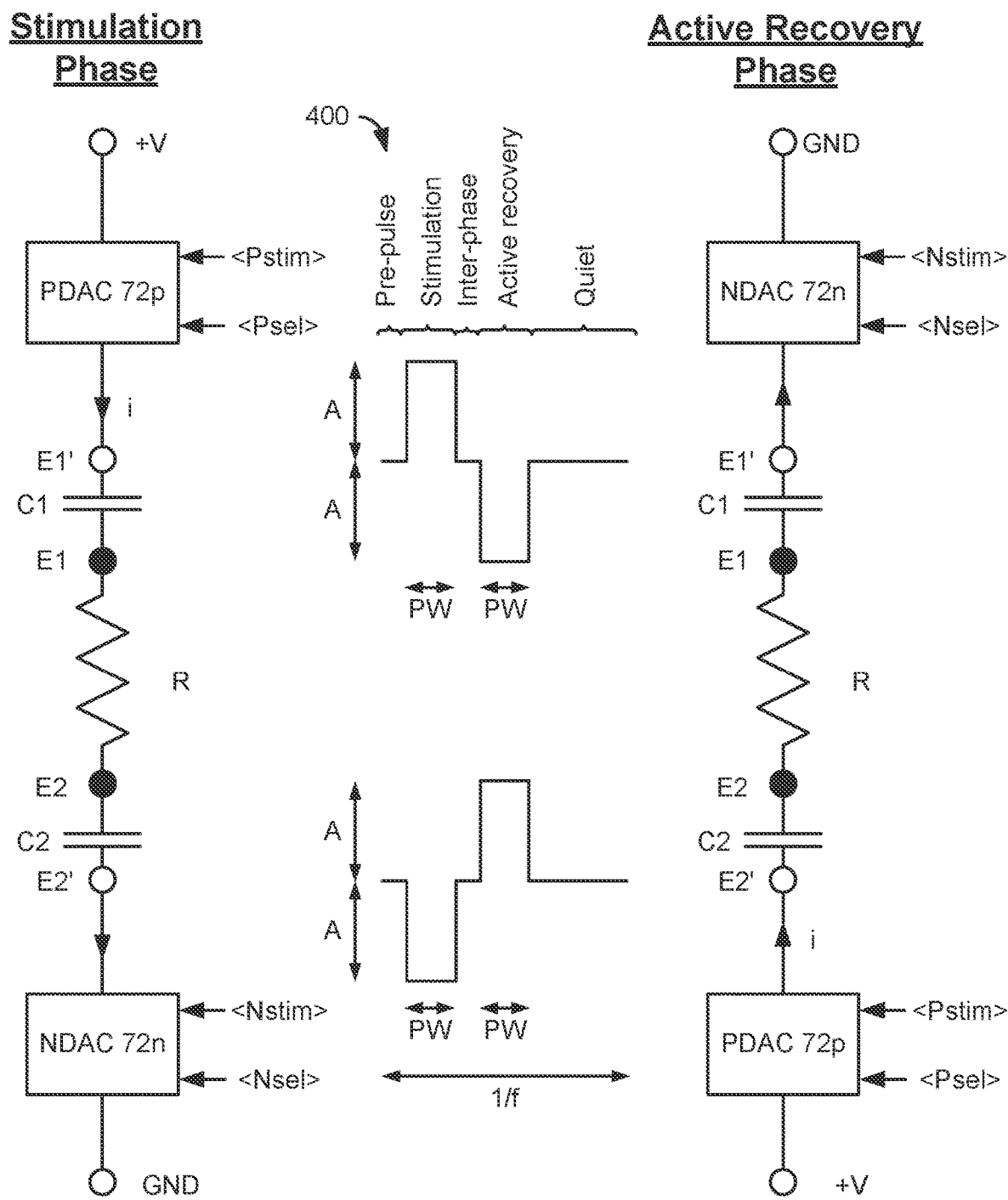
FIG. 4 shows an example of the configuration of stimulation circuitry to form an example biphasic square wave pulse in accordance with an example of the disclosure.

The stimulation programs that are communicated to the IPG 10 include stimulation parameters that are ultimately converted to control signals that are distributed to one or more Digital-to-Analog Converters (DACs) 72 in the IPG 10's stimulation circuitry to provide electrical stimulation to the patient via one or more selected electrodes that are connectable to the IPG 10. FIG. 4 shows a simple example of DAC circuitry 72 as arranged to provide a typical biphasic square wave pulse 400 at selected electrodes E1 and E2, through a patient's tissue, R. DAC circuitry 72 as shown comprises two portions, denoted as PDAC 72p and NDAC 72n. These portions of DAC circuitry 72 are so named due to the polarity of the transistors used to build them and the polarity of the current they provide. Thus, PDAC 72p is formed from P-channel transistors and is used to source a current +I to the patient's tissue R via a selected electrode operating as an anode. NDAC 72n is formed of N-channel transistors and is used to sink current −I from the patient's tissue via a selected electrode operating as a cathode. It is important that current sourced to the tissue at any given time equal that sunk from the tissue to prevent charge from building in the tissue, although more than one anode electrode and more than one cathode electrode may be operable at a given time.

PDAC 72p and NDAC 72n are current sources that receive digital control signals, denoted <Pstim> and <Nstim> respectively, to generate current of a prescribed amplitude at appropriate times. More specifically, PDAC 72p and NDAC 72n include current-mirrored transistors for mirroring (amplifying) a reference current Iref to produce pulses with a specified amplitude. Although the DAC circuitry 72 (PDAC 72p and NDAC 72n) may be dedicated at each of the electrodes and thus may be activated only when its associated electrode is to be selected as an anode or cathode, see, e.g., U.S. Pat. No. 6,181,969, the illustrated example assumes that one or more DACs (or one or more current sources within a DAC) are distributed to a selected electrode by a switch matrix (not shown), and control signals <Psel> and <Nsel> are used to control the switch matrix and establish the connection between the selected electrode and the PDAC 72p or NDAC 72n.

In the example shown, control signals <Pstim> and <Nstim> and <Psel> and <Nsel> prescribe the various parameters of the biphasic square wave pulse 400. The pulse 400 is defined by multiple phases that include a pre-pulse phase, a stimulation phase, an inter-phase phase, an active recovery phase, and a quiet phase. In the illustrated example, during the pre-pulse phase, the inter-phase phase, and the quiet phase, no current is passed through the tissue R and thus the PDAC 72p and NDAC 72n are inactive (or at least not coupled to any electrode). During the stimulation phase, current I (having amplitude A) is sourced from the PDAC 72p to electrode node E1' (a node in the IPG 10's current generation circuitry that is coupled to electrode E1 through a blocking capacitor C1) for a duration PW. From electrode node E1', the current I flows through the blocking capacitor C1 to the electrode E1. The NDAC 72n pulls the current I through the patient's tissue R from electrode E2 through the blocking capacitor C2 and to the electrode node E2' over the same duration PW. During the active recovery phase, DAC circuitry 72 is reversed such that current I (again having amplitude A in the example shown) is sourced from the PDAC '72p to electrode node E2' for a duration PW. From electrode node E2', the current I flows through the blocking capacitor C2 to the electrode E2, and the NDAC 72n pulls the current I through the patient's tissue R from electrode E1 through the blocking capacitor C1 and to the electrode node E1' over the same duration PW. In each of the stimulation and active recovery phases, the PDAC 72p and NDAC 72n along with the intervening tissue R complete a circuit between a power supply +V and ground. The compliance voltage +V is adjustable to an optimal level to ensure that current pulses of a prescribed amplitude can be produced without unnecessarily wasting IPG power. While a single period of the pulse 400 is illustrated, a stimulation program may typically specify that the pulse 400 is to be repeated in succession, and the duration of the single period of the pulse 400 defines the stimulation frequency f.

Figure 5A:
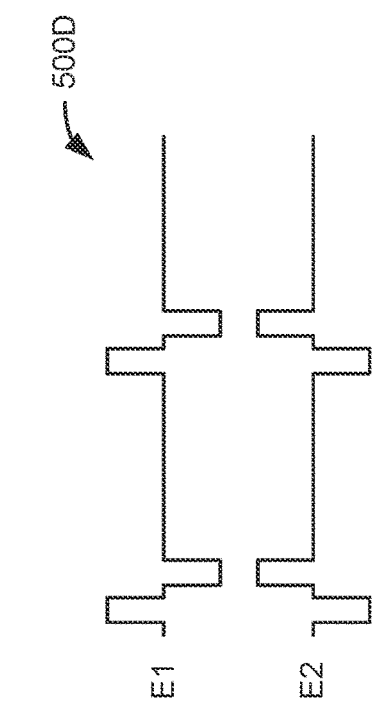
FIGS. 5A-5E illustrate example waveforms that are defined by stimulation programs that specify a periodic application of biphasic square wave pulses having different parameters in accordance with examples of the disclosure.
Figure 5B:
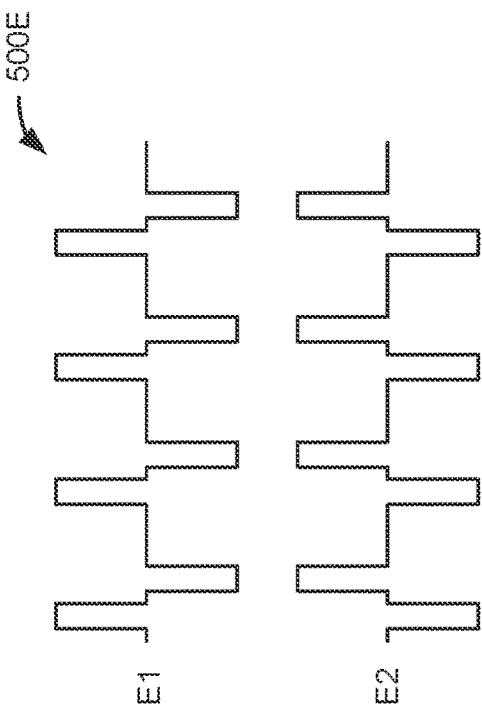
Figure 5D:
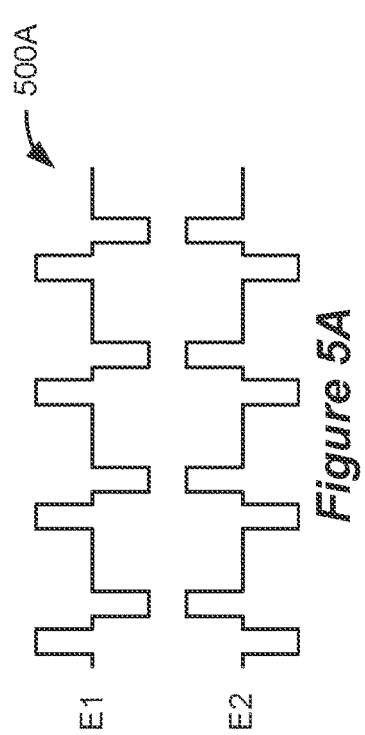
Figure 5E:
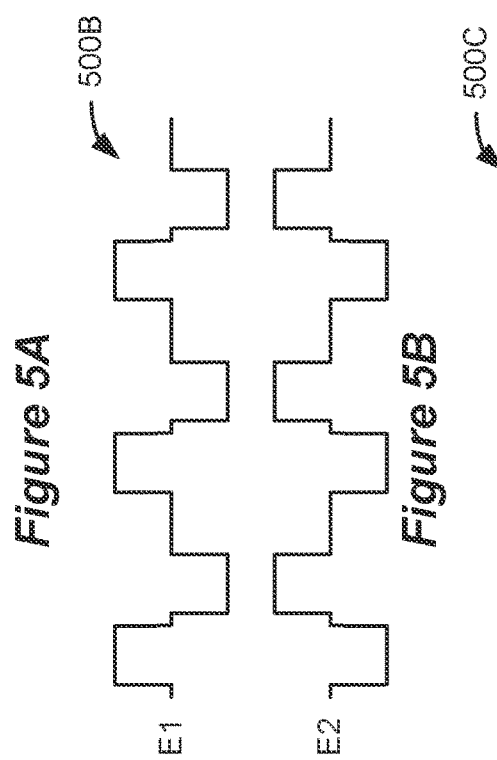
Figure 5C:
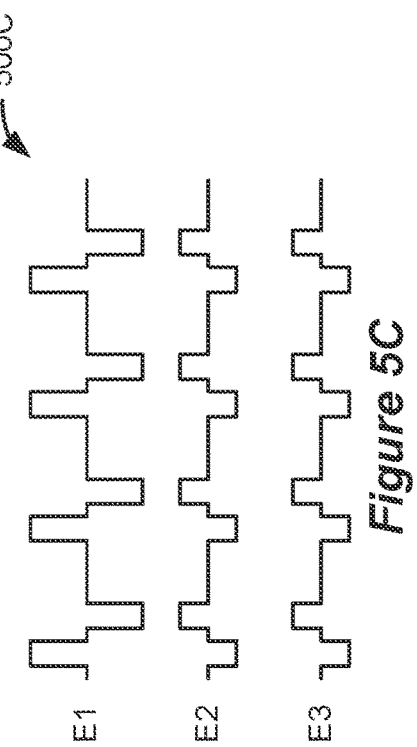

FIGS. 5A-5E show example waveforms that are defined by different stimulation programs that specify different parameters for biphasic square wave pulses. FIG. 5A shows a waveform that is defined by an example stimulation program 500A according to which pulse 400 is periodically applied between electrodes E1 and E2. FIG. 5B shows a waveform that is defined by an example stimulation program 500B according to which a modified version of pulse 400 that includes a longer pulse width (i.e., a longer duration of the stimulation and active recovery phases) is periodically applied between electrodes E1 and E2. FIG. 5C shows a waveform that is defined by an example stimulation program 500C in which pulse 400 is periodically applied with electrode E1 receiving all of the stimulation anodic current (i.e., the anodic current during the stimulation phase) and electrodes E2 and E3 receiving equal portions of the stimulation cathodic current (i.e., the cathodic current during the stimulation phase). FIG. 5D shows a waveform that is defined by an example stimulation program 500D in which a modified version of pulse 400 that includes a longer quiet phase is applied periodically between electrodes E1 and E2. FIG. 5E shows a waveform that is defined by an example stimulation program 500E in which a modified version of pulse 400 that includes a higher-amplitude current in the stimulation and active recovery phases is applied periodically between electrodes E1 and E2. As can be seen from these few examples, a large number of different waveforms can be defined through simple modifications of the parameters of biphasic square wave pulses, and each of the different waveforms may elicit different sensations in the patient.

Figure 6A:
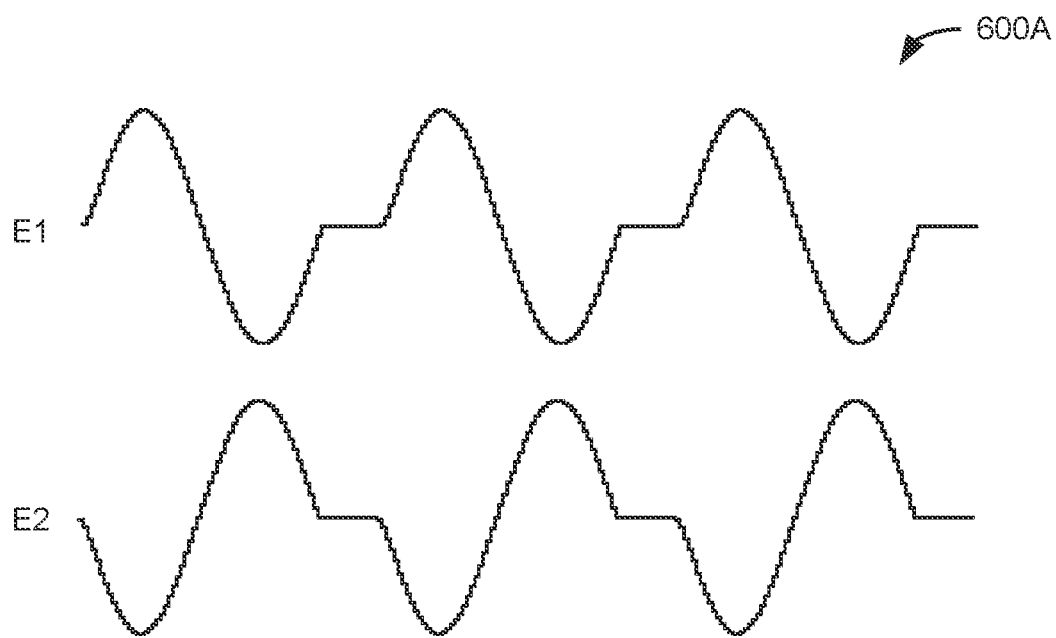
FIGS. 6A and 6B illustrate more complex waveforms that are defined by stimulation programs in accordance with examples of the disclosure.
Figure 6B:
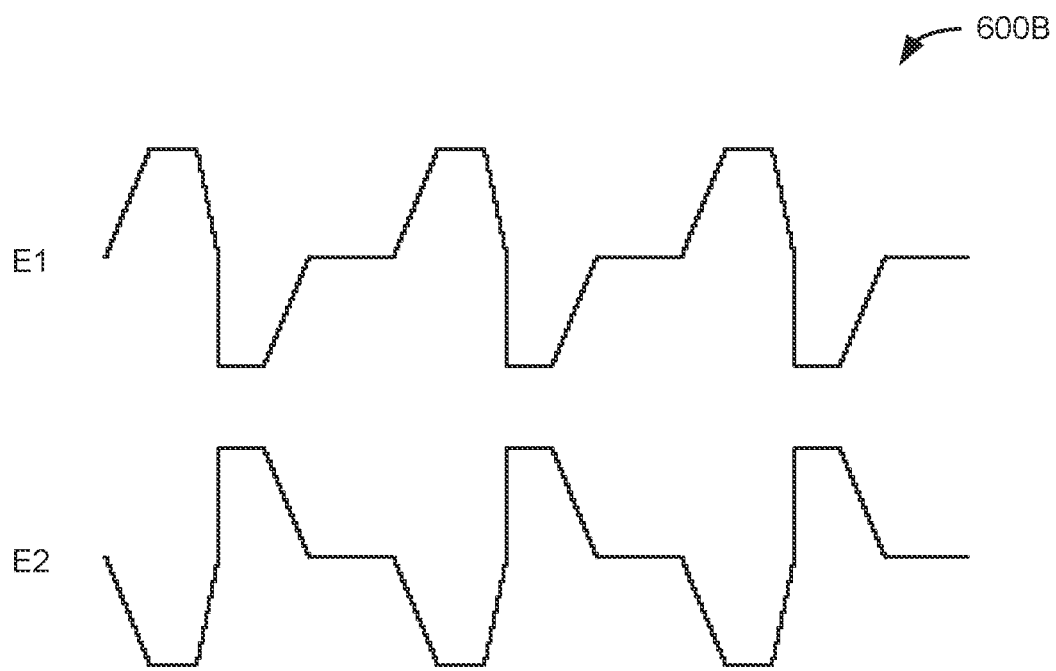

In addition to the numerous stimulation programs that can be created via modifications to parameters of standard biphasic square wave pulses, some IPGs 10 are configurable to create more arbitrary waveforms as described in US Patent Publication No. 2018/0071513. FIGS. 6A and 6B illustrate example stimulation programs that involve more complex waveforms. FIG. 6A shows a sinusoidal type waveform with a subsequent quiet phase that is periodically applied between electrodes E1 and E2 as defined by an example stimulation program 600A. FIG. 6B shows a saw tooth waveform that is periodically applied between electrodes E1 and E2 as defined by an example stimulation program 600B.

As can be appreciated from the examples shown, the number of different types of stimulation programs that can be created is practically limitless. Such various different stimulation programs may provide different sensations and different types of pain relief to a patient. For example, various different stimulation programs may provide sub-threshold stimulation (i.e., stimulation that does not produce a side effect such as paresthesia but nonetheless provides pain relief) while others provide super-threshold stimulation (i.e., stimulation that provides pain relief via or in addition to paresthesia). Similarly, a particular stimulation program may provide effective pain relief at a particular point in time or during a particular patient activity while a different stimulation program may provide more effective pain relief at a different point in time or during a different patient activity.

As noted above, it is therefore typical for stimulation parameters that define a number of different stimulation programs having different properties (e.g., different amplitudes, pulse widths, frequencies, waveform shapes, selected electrodes, etc.) to be configured at an external device (e.g., via the CP GUI 94 or the external controller 40) and then sent to and stored on the IPG 10 (e.g., in memory comprising the IPG 10's control circuitry) where each stimulation program defines a waveform to be formed at a set of electrodes. This process of configuring stimulation programs such that they may be stored on the IPG 10 may occur during the trial stimulation phase (e.g., stimulation programs may be configured for execution by the external trial stimulator and those that prove promising may be transferred to the IPG 10) or at any time after implantation of the IPG 10. New stimulation programs may additionally be created and stored on the IPG 10 by modifying existing stimulation programs that are stored on the IPG 10. As noted above, the stimulation programs may provide different types of pain relief and the patient may find different programs to be most effective in different situations. Thus, the patient can select (e.g., via external controller 40) a desired one of the pre-configured stimulation programs to be executed at a particular time or, if the IPG 10 allows it, multiple ones of the stimulation programs to be executed simultaneously.

Figure 7:
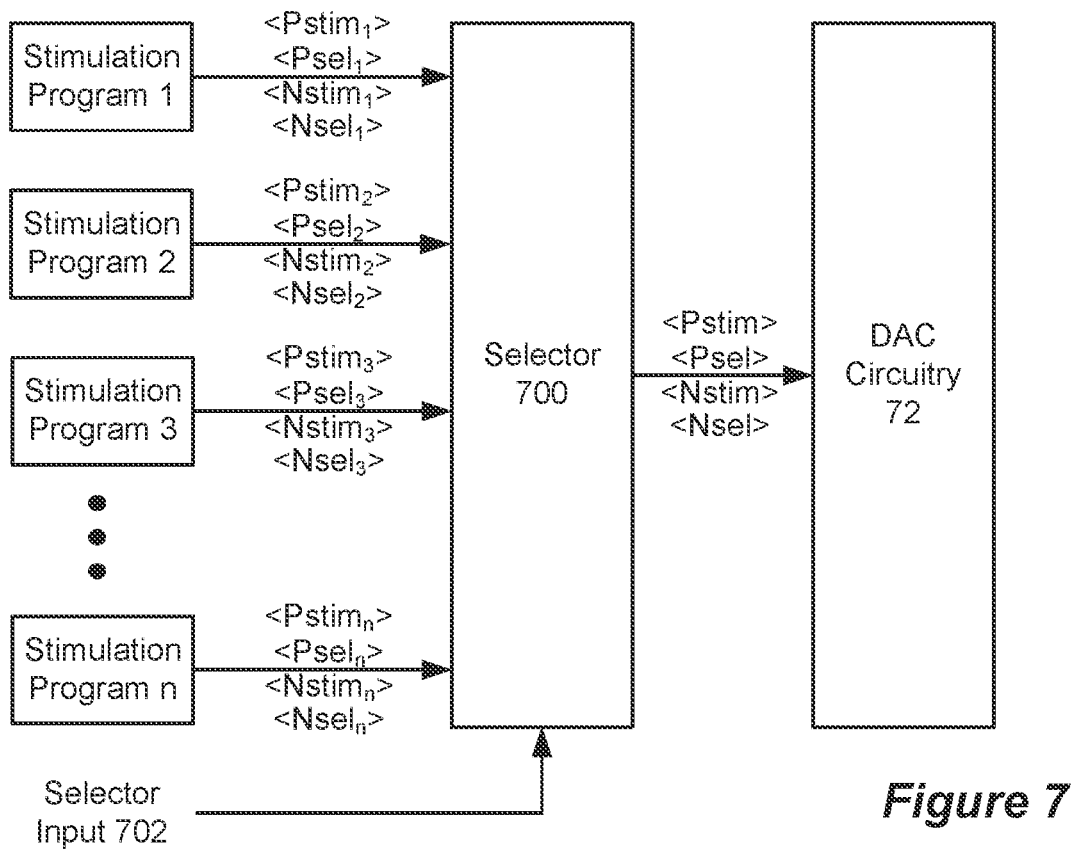
FIG. 7 is a block diagram that illustrates a selector for passing control signals to stimulation circuitry in accordance with an input that specifies a time domain allocation between stimulation programs in accordance with an example of the disclosure.

The inventor recognizes that it would be beneficial to enable a patient to transition between configured stimulation programs or to select some combination of the configured stimulation programs, as opposed to any one stimulation program itself, as the therapy to be delivered. FIG. 7 illustrates a selector 700 that enables precise control of the control signals that are ultimately passed to the DAC circuitry 72. The selector 700, which may be implemented as part of the IPG 10's microcontroller or other control circuitry, selects the control signals corresponding to a particular stimulation program to be forwarded to the DAC circuitry 72 at a particular time according to a selector input 702. The selector input 702 is received by the selector 700 and specifies the two or more stimulation programs that are selected for execution and the time domain allocation of the selected stimulation programs. While each of the stimulation programs is independently executable, the selector 700 enables different selected stimulation programs to be interleaved in time according to the time domain allocation that is specified by the input 702. Specifically, the waveforms that are formed through the interleaving of stimulation programs by selector 700 are formed in a single timing channel. This is different, and more convenient, than forming different stimulation programs in different timing channels. Plus, interleaving the stimulation programs in a single timing channel frees the other timing channels in the IPG 10, which may now be used to provide other stimulation, therefore allowing more complex therapies to be provided to the patient. Use of timing channels in an IPG is discussed further in U.S. Pat. Nos. 6,516,227 and 9,656,081.

Figure 8:
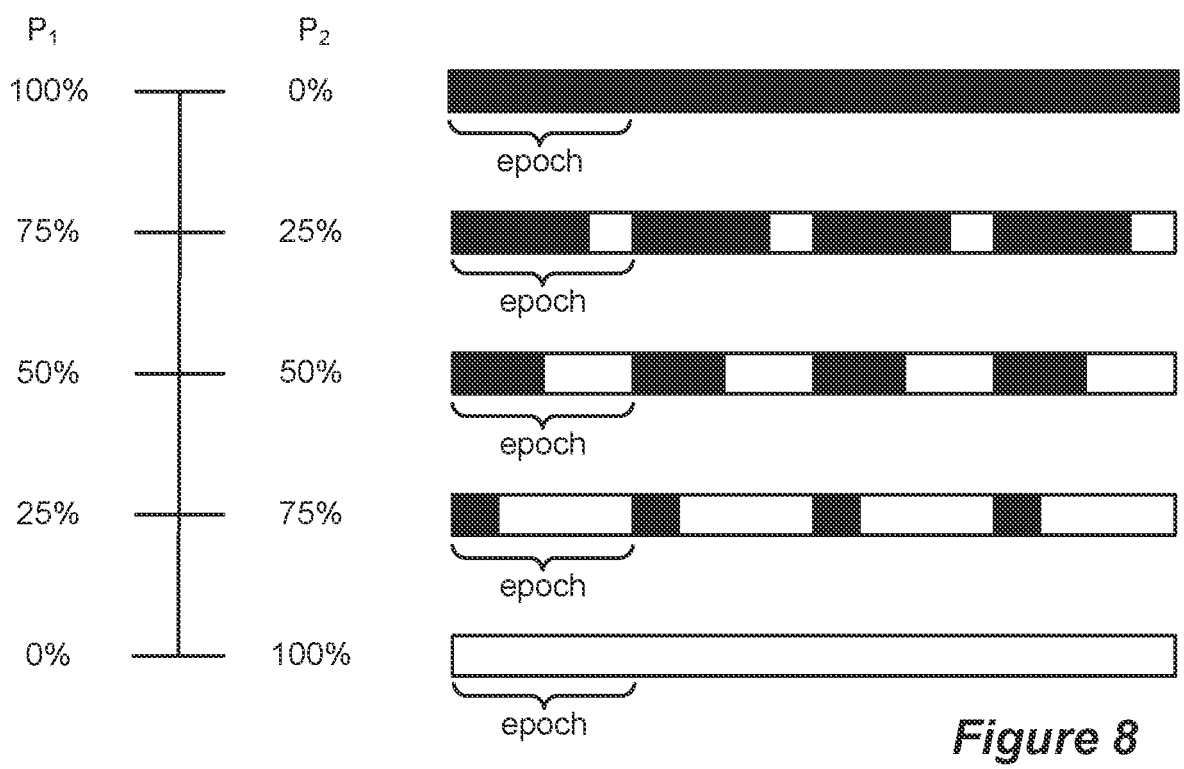
FIG. 8 illustrates the proportion of time that is allocated to each of two stimulation programs within repeating epochs for different time domain allocations between the stimulation programs in accordance with an example of this disclosure.

FIG. 8 shows an example of the time domain allocation of two selected stimulation programs. In the illustrated example, the selector 700's output is divided into equal duration epochs. Within each epoch, the selector 700 passes the control signals corresponding to a first stimulation program (P1 in the example) for a first portion of the epoch and the control signals corresponding to a second stimulation program (P2 in the example) for a second portion of the epoch. The durations of the first and second portions of the epoch are determined based on the time domain allocation of the stimulation programs as set by the input 702. For example, the proportion of each stimulation program's time period within an epoch is equal to the stimulation program's time domain allocation as set by the input 702. The duration of each epoch may be a user-definable property. In one embodiment, an epoch may be between 100 microseconds and several hours in length, but this duration may be altered depending on the selected stimulation programs and the patient's desires.

Figure 9:
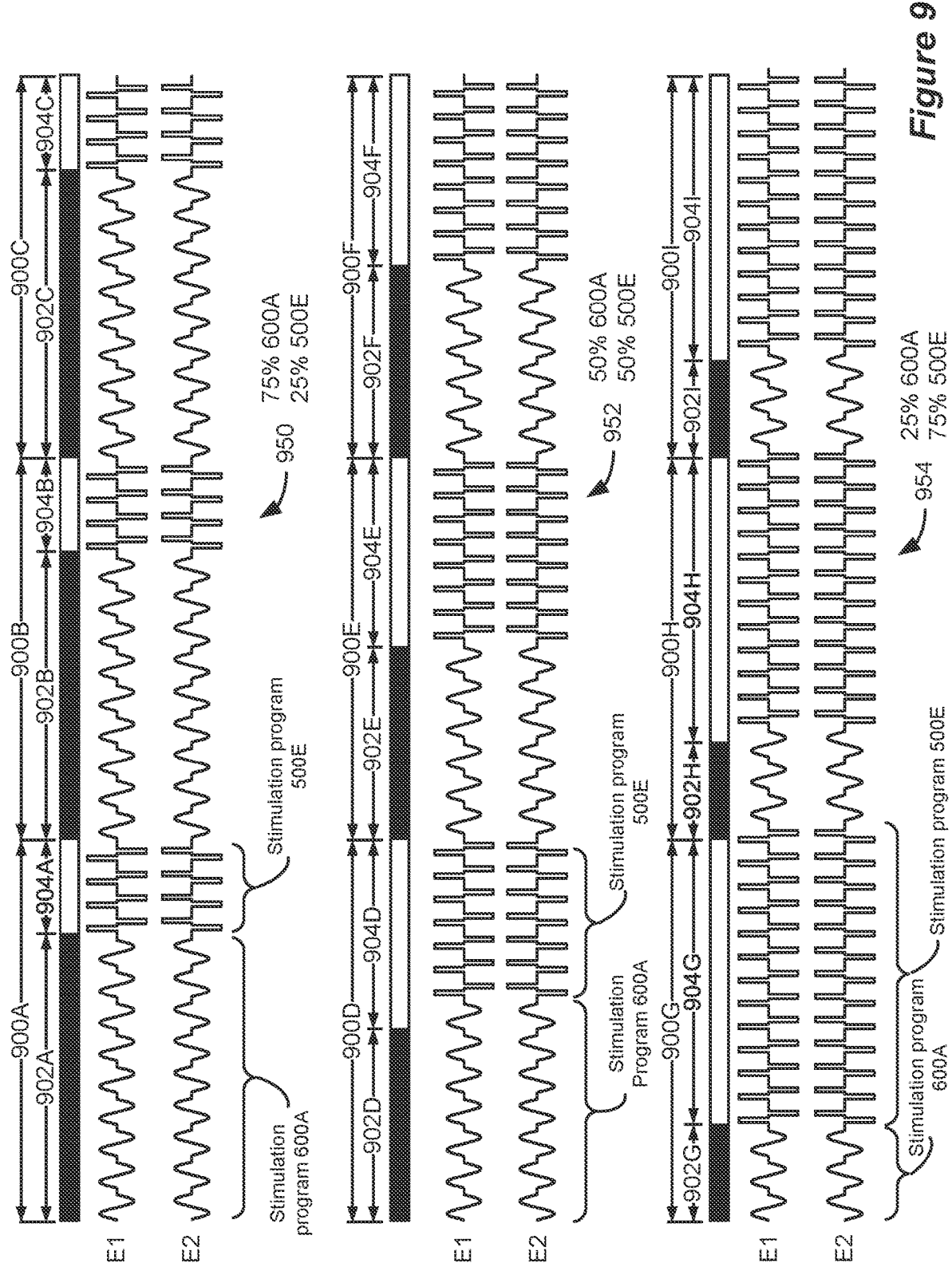
FIG. 9 illustrates the waveforms formed at two selected electrodes for different time domain allocations of two stimulation programs in accordance with an example of this disclosure.

FIG. 9 shows an example of the waveform that is formed at electrodes E1 and E2 for different time domain allocations of stimulation programs 600A and 500E using the epoch technique that is illustrated in FIG. 8. As described above, stimulation program 500E defines a periodic application of a biphasic square wave pulse and stimulation program 600A defines a periodic application of a sinusoidal pulse. In addition to their different pule shapes, the pulses associated with stimulation program 500E are applied at a greater frequency and have a greater amplitude than the pulses associated with stimulation program 600A, so the stimulation programs 500E and 600A may provide different sensations and types of pain relief to the patient. In the top portion 950 of FIG. 9, the input 702 specifies a time domain allocation of 75% for stimulation program 600A and 25% for stimulation program 500E. Within each epoch 900, the selector 700 passes the control signals corresponding to stimulation program 600A to the DAC circuitry 72 during a first period 902 that has a duration equal to 75% of the total duration of the epoch 900 and passes the control signals corresponding to stimulation program 500E to the DAC circuitry 72 during a second period 904 that has a duration equal to 25% of the total duration of the epoch 900. As a result, the waveform corresponding to stimulation program 600A is formed at electrodes E1 and E2 during periods 902 and the waveform corresponding to stimulation program 500E is formed at electrodes E1 and E2 during periods 904. This time domain allocation between the stimulation programs 600A and 500E is repeated for each epoch 900 while the input 702 is held at the same value.

In the middle portion 952 of FIG. 9, the input 702 specifies a time domain allocation of 50% for stimulation program 600A and 50% for stimulation program 500E. Within each epoch 900, the selector 700 passes the control signals corresponding to stimulation program 600A to the DAC circuitry 72 during a first period 902 that has a duration equal to 50% of the total duration of the epoch 900 and passes the control signals corresponding to stimulation program 500E to the DAC circuitry 72 during a second period 904 that has a duration equal to 50% of the total duration of the epoch 900. As a result, the waveform corresponding to stimulation program 600A is formed at electrodes E1 and E2 during periods 902 and the waveform corresponding to stimulation program 500E is formed at electrodes E1 and E2 during periods 904. This time domain allocation between the stimulation programs 600A and 500E is repeated for each epoch 900 while the input 702 is held at the same value.

As illustrated in this middle portion 952 of FIG. 9, when an active pulse is ongoing at the end of a stimulation program's time period (as shown at the end of time period 902D, for example), the pulse is completed before the selector 700 switches to the other stimulation program. This can result in a pulse corresponding to a first stimulation program being completed during the time period allocated to another stimulation program and an unequal number of pulses in different ones of a stimulation program's time periods. In an alternate embodiment, the selector 700 may determine whether a pulse corresponding to a stimulation program can be completed within the stimulation program's allocated time period and, if not, can either immediately begin passing the control signals for the subsequent time period's stimulation program to the DAC circuitry 72 or simply delay any further stimulation until the start of the subsequent time period. In another alternate embodiment, the selector 700 can simply complete the current phase of the active pulse (rather than the complete pulse) and then immediately begin passing the control signals for the subsequent time period's stimulation program to the DAC circuitry 72. In yet another embodiment, the time period may be extended to accommodate the final pulse such that the pulse does not use some of the subsequent time period.

In the bottom portion 954 of FIG. 9, the input 702 specifies a time domain allocation of 25% for stimulation program 600A and 75% for stimulation program 500E. Within each epoch 900, the selector 702 passes the control signals corresponding to stimulation program 600A to the DAC circuitry 72 during a first period 902 that has a duration equal to 25% of the total duration of the epoch 900 and passes the control signals corresponding to stimulation program 500E to the DAC circuitry 72 during a second period 904 that has a duration equal to 75% of the total duration of the epoch 900. As a result, the waveform corresponding to stimulation program 600A is formed at electrodes E1 and E2 during periods 902 and the waveform corresponding to stimulation program 500E is formed at electrodes E1 and E2 during periods 904. This time domain allocation between the stimulation programs 600A and 500E is repeated for each epoch 900 while the input 702 is held at the same value.

As illustrated in the example in FIG. 9, the selector 700 enables a patient to transition smoothly from a first stimulation program (e.g., stimulation program 600A) to a second stimulation program (e.g., stimulation program 500E) over time or to create a hybrid stimulation program by interleaving pre-configured stimulation programs according to a desired time domain allocation. In one embodiment, a hybrid stimulation program that is created through the use of the selector 700 can be stored on the IPG as a separate stimulation program.

Figure 10:
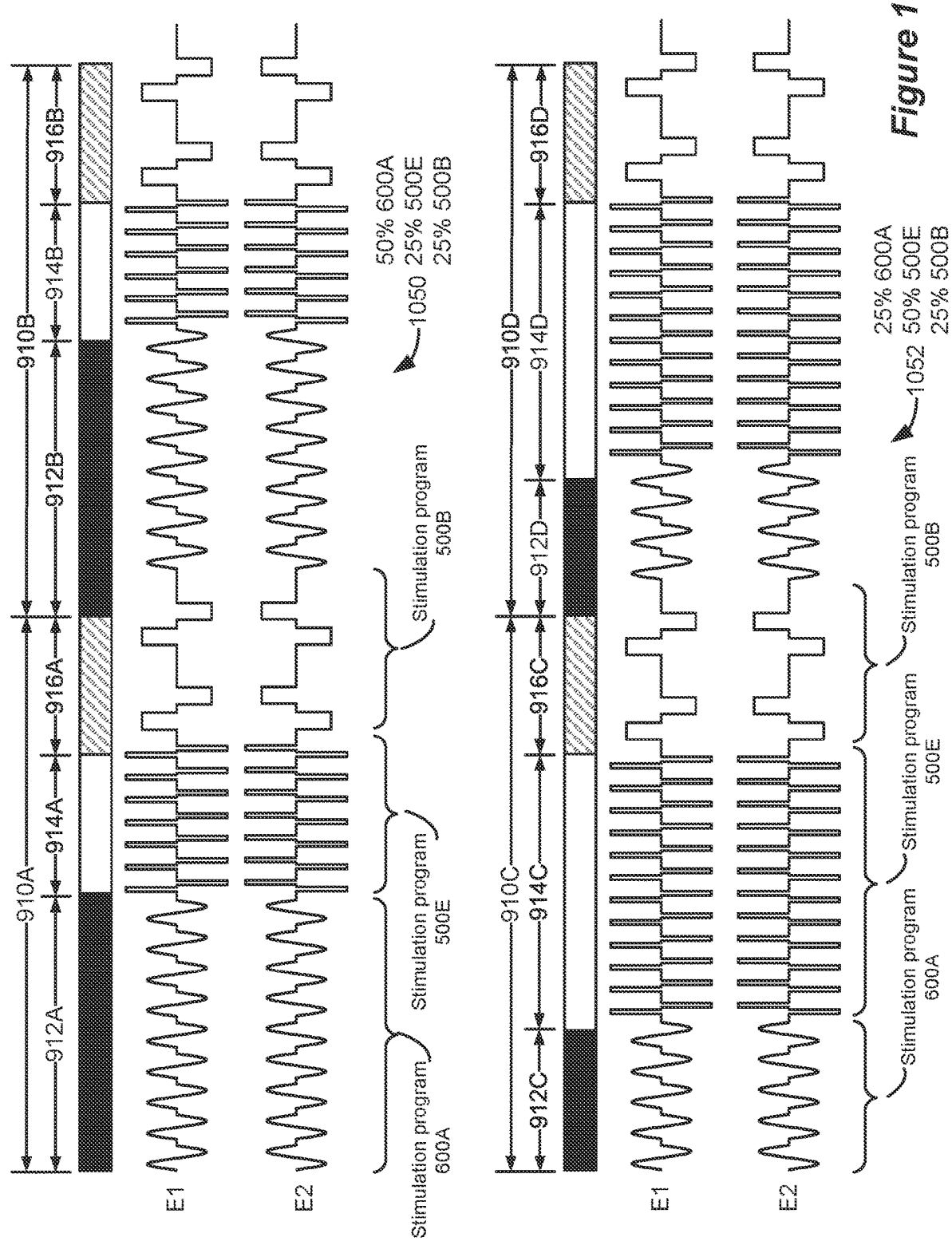
FIG. 10 illustrates the waveforms formed at two selected electrodes for different time domain allocations of three stimulation programs in accordance with an example of this disclosure.

While FIG. 9 illustrates an example of the epoch technique for allocating time to each of two selected stimulation programs that both utilize the same electrodes, the epoch technique can also be utilized for allocating time between a greater number of stimulation programs and stimulation programs that utilize different electrodes. FIG. 10 shows an example of the stimulation waveform that is formed at electrodes E1 and E2 for different time domain allocations of stimulation programs 600A, 500E, and 500B using the epoch technique. In the top portion 1050 of FIG. 10, the input 702 specifies a time domain allocation of 50% for stimulation program 600A, 25% for stimulation program 500E, and 25% for stimulation program 500B. As with the example in FIG. 9, within each epoch 910, the selector 700 passes the control signals corresponding to stimulation program 600A to the DAC circuitry 72 during a first period 912 that has a duration equal to 50% of the total duration of the epoch 910, passes the control signals corresponding to stimulation program 500E to the DAC circuitry 72 during a second period 914 that has a duration equal to 25% of the total duration of the epoch 910, and passes the control signals corresponding to stimulation program 500B to the DAC circuitry 72 during a third period 916 that has a duration equal to 25% of the total duration of the epoch 910. As a result, the waveform corresponding to stimulation program 600A is formed at electrodes E1 and E2 during periods 912, the waveform corresponding to stimulation program 500E is formed at electrodes E1 and E2 during periods 914, and the waveform corresponding to stimulation program 500B is formed at electrodes E1 and E2 during periods 916.

In the bottom portion 1052 of FIG. 10, the input 702 specifies a time domain allocation of 25% for stimulation program 600A, 50% for stimulation program 500E, and 25% for stimulation program 500B. The selector 700 passes the control signals corresponding to stimulation program 600A to the DAC circuitry 72 during a first period 912 that has a duration equal to 25% of the total duration of the epoch 910, passes the control signals corresponding to stimulation program 500E to the DAC circuitry 72 during a second period 914 that has a duration equal to 50% of the total duration of the epoch 910, and passes the control signals corresponding to stimulation program 500B to the DAC circuitry 72 during a third period 916 that has a duration equal to 25% of the total duration of the epoch 910. As a result, the waveform corresponding to stimulation program 600A is formed at electrodes E1 and E2 during periods 912, the waveform corresponding to stimulation program 500E is formed at electrodes E1 and E2 during periods 914, and the waveform corresponding to stimulation program 500B is formed at electrodes E1 and E2 during periods 916.

Figure 11:
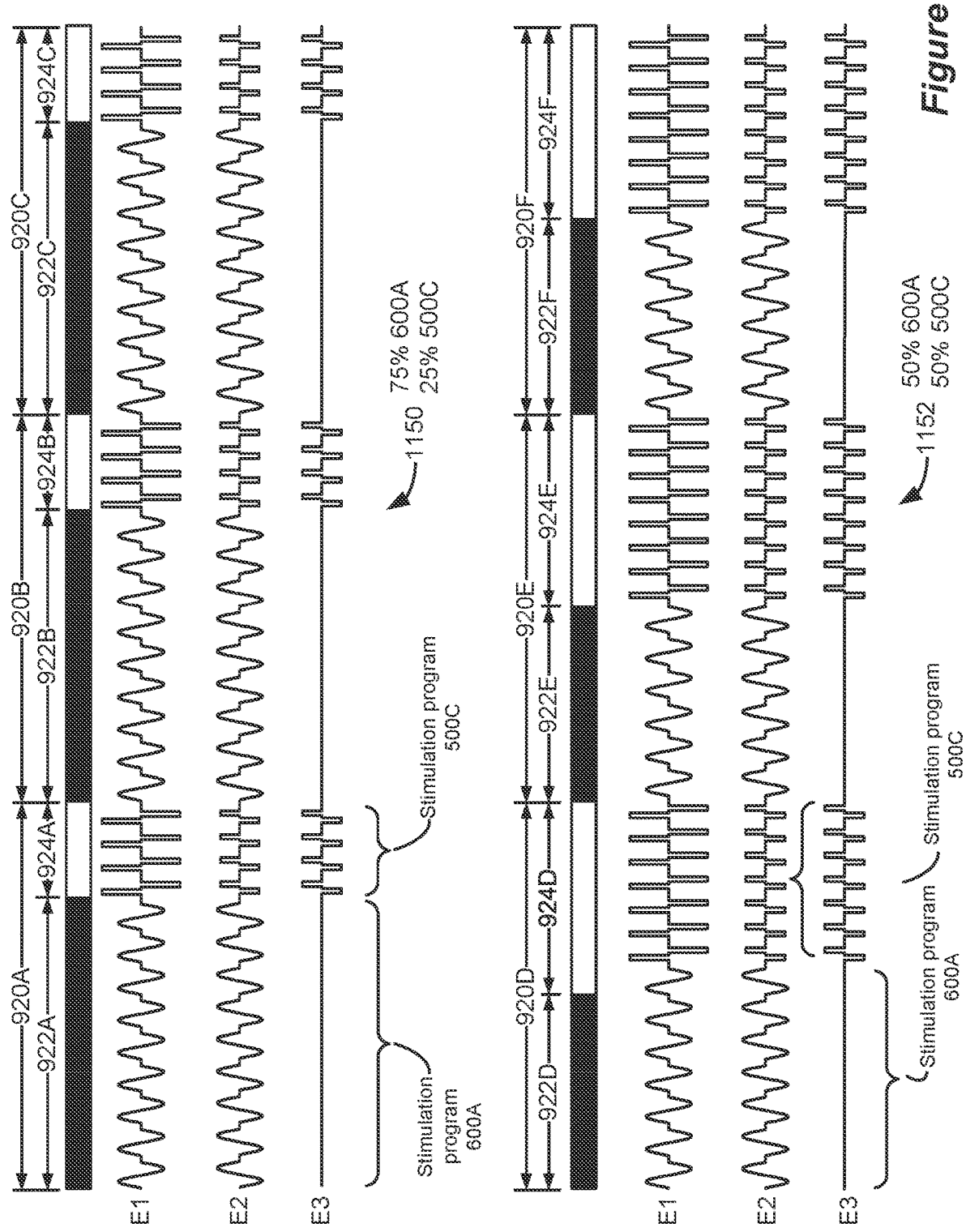
FIG. 11 illustrates the waveforms formed at three selected electrodes for different time domain allocations of two stimulation programs in accordance with an example of this disclosure.

FIG. 11 shows an example of the stimulation waveform that is formed at electrodes E1, E2, and E3 for different time domain allocations of stimulation programs 600A and 500C. In the top portion 1150 of FIG. 11, the input 702 specifies a time domain allocation of 75% for stimulation program 600A and 25% for stimulation program 500C, and the selector 700 passes the control signals corresponding to stimulation program 600A to the DAC circuitry 72 during a first period 922 that has a duration equal to 75% of the total duration of the epoch 920 and passes the control signals corresponding to stimulation program 500C to the DAC circuitry 72 during a second period 924 that has a duration equal to 25% of the total duration of the epoch 920. Because stimulation program 500C specifies that cathodic stimulation current is split equally between electrodes E2 and E3, electrodes E1, E2, and E3 are active during the periods 924. In the bottom portion 1152 of FIG. 11, the input 702 specifies a time domain allocation of 50% for stimulation program 600A and 50% for stimulation program 500C, and the selector 702 passes the control signals corresponding to stimulation program 600A to the DAC circuitry 72 during a first period 922 and passes the control signals corresponding to stimulation program 500C to the DAC circuitry 72 during a second period 924. Here again, electrodes E1, E2, and E3 are active during the periods 924.

Up to this point, the example stimulation programs have specified a continuous periodic application of a waveform with a relatively short period such that multiple periods are executable even within an epoch of a short duration. This type of interleaving may be referred to as a re-initiate mode of operation, because each stimulation program is simply re-initiated during each of its time allocations. However, stimulation programs may also define more complex stimulation patterns with waveforms of different types, and the various types of waveforms may extend over a longer duration such that the stimulation program cannot be executed within its allocated portion of an epoch.

Figure 12:
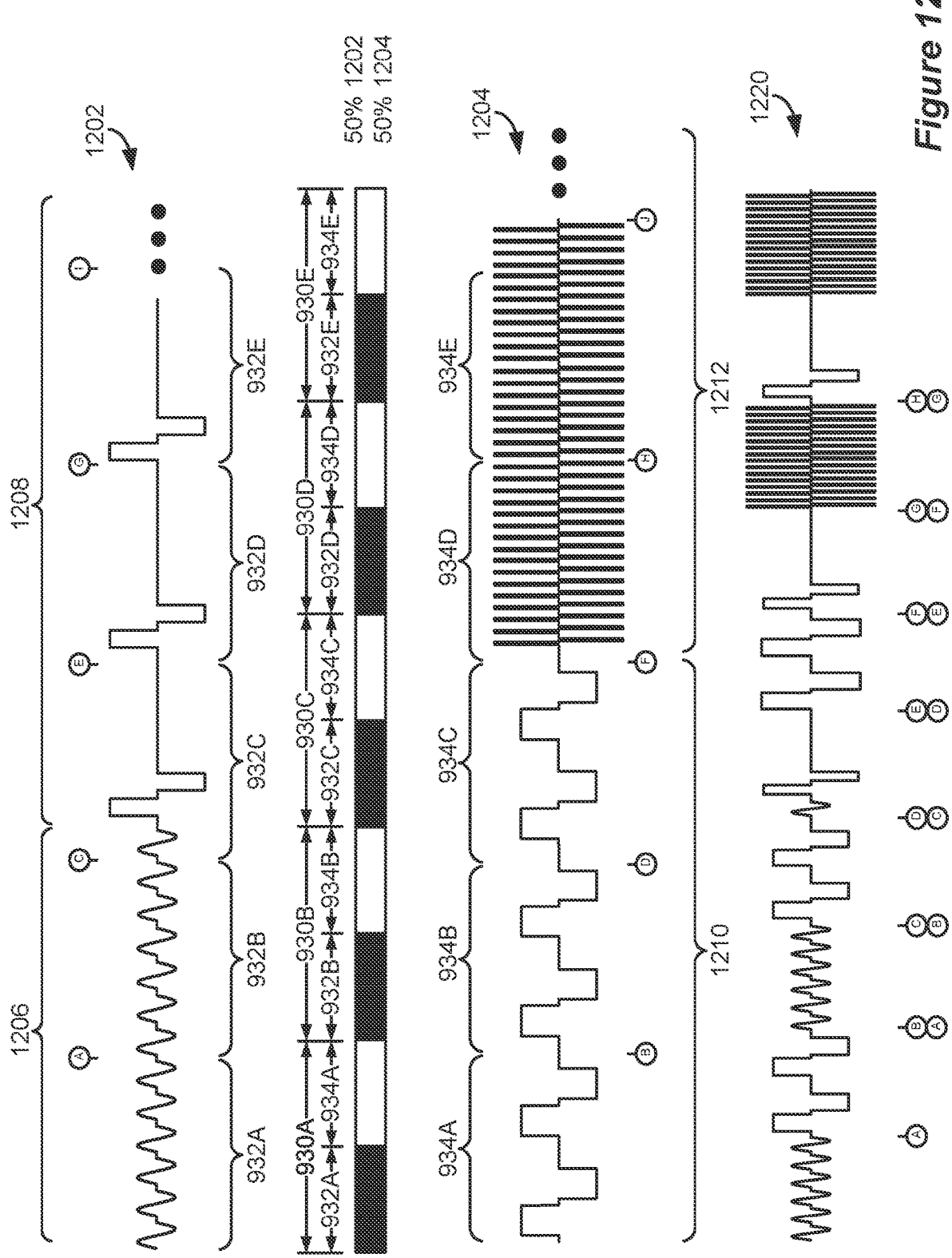
FIG. 12 illustrates an example waveform that is formed for a bookmarking time domain allocation mode of operation for two stimulation programs in accordance with an example of this disclosure.

FIG. 12 shows waveforms that are defined by two different examples of complex stimulation programs 1202 and 1204 and the manner in which such complex stimulation programs might be interleaved in accordance with a bookmarking mode of operation using the epoch technique. The first stimulation program 1202 defines a periodic application of a sinusoidal wave for a number of periods (1206) followed by a periodic application of a biphasic square wave having a greater amplitude and a long quiet period for a number of periods (1208). The second stimulation program 1204 defines a periodic application of a biphasic square wave with a larger pulse width for a number of periods (1210) followed by a periodic application of a biphasic square wave having a greater amplitude and a higher frequency for a number of periods (1212). In the example shown in FIG. 12, the input 702 specifies a time domain allocation of 50% for stimulation program 1202 and 50% for stimulation program 1204, and the selector 700 passes the control signals corresponding to stimulation program 1202 to the DAC circuitry 72 during first periods 932 that each have a duration equal to 50% of the total duration of the epoch 930 and passes the control signals corresponding to stimulation program 1204 to the DAC circuitry 72 during second periods 934 that each have a duration equal to 50% of the total duration of the epoch 930.

Because neither stimulation program can be executed completely within a single one of its associated time periods, the bookmark mode of operation specifies that a position should be stored at an end of each stimulation program's respective time allocation to mark a beginning position in a subsequent time allocation. In the illustrated example, stimulation program 1202 is executed during time period 932A, and, at the end of the time period 932A, the current position (i.e., the portion of the stimulation program 1202 that is being executed at the end of the time period 932A) within the stimulation program 1202 is bookmarked (as denoted by the bookmark labeled "A"). Stimulation program 1204 is then executed during time period 934A, and, at the end of time period 934A, the current position within the stimulation program 1204 is bookmarked (as denoted by the bookmark labeled "B"). When the time period 934A ends, the selector 700 switches back to stimulation program 1202 and passes control signals that correspond to the bookmarked position (i.e., the bookmark labeled "A"). Stimulation continues from that bookmarked position according to the stimulation parameters defined by stimulation program 1202 during the time period 932B, and, at the end of the time period 932B, the current position within the stimulation program 1202 is again bookmarked (as denoted by the bookmark labeled "C"). The selector 700 then similarly switches back to stimulation program 1204 and passes control signals that correspond to the bookmarked position (i.e., the bookmark labeled "B").

As illustrated by the resulting waveform 1220 (which is shown using a different timescale than the waveforms of its constituent stimulation programs and only one polarity), this process of switching back and forth between bookmarked positions of the stimulation programs 1202 and 1204 is continued in succeeding epochs 930. If a stimulation program specifies a repeating application of a defined waveform as is typical, the selector 700 will loop back to the beginning of the waveform in the time period during which the end of the waveform is reached and stimulation will continue. While the example illustrates two stimulation programs with a time domain allocation of 50% for each, it will be understood that the same technique is applicable to larger numbers of stimulation programs and different time domain allocations by adjusting the number and duration of the time periods within an epoch in the same manner as described above. While not specifically addressed in the example in FIG. 12, it will also be understood that the selector 700 may negotiate the switching process such that switching occurs when no current is being delivered in the same manners as described above.

The bookmark location of a stimulation program can be specified and saved in different ways. In a first embodiment, the bookmark location is specified as a timestamp that corresponds to the location in the stimulation program. In another embodiment, the bookmark location is specified as a number of the particular phase within the particular pulse that corresponds to the location in the stimulation program. As will be understood, the bookmark location can also be specified in other ways that identify a location within a stimulation program.

Figure 13:
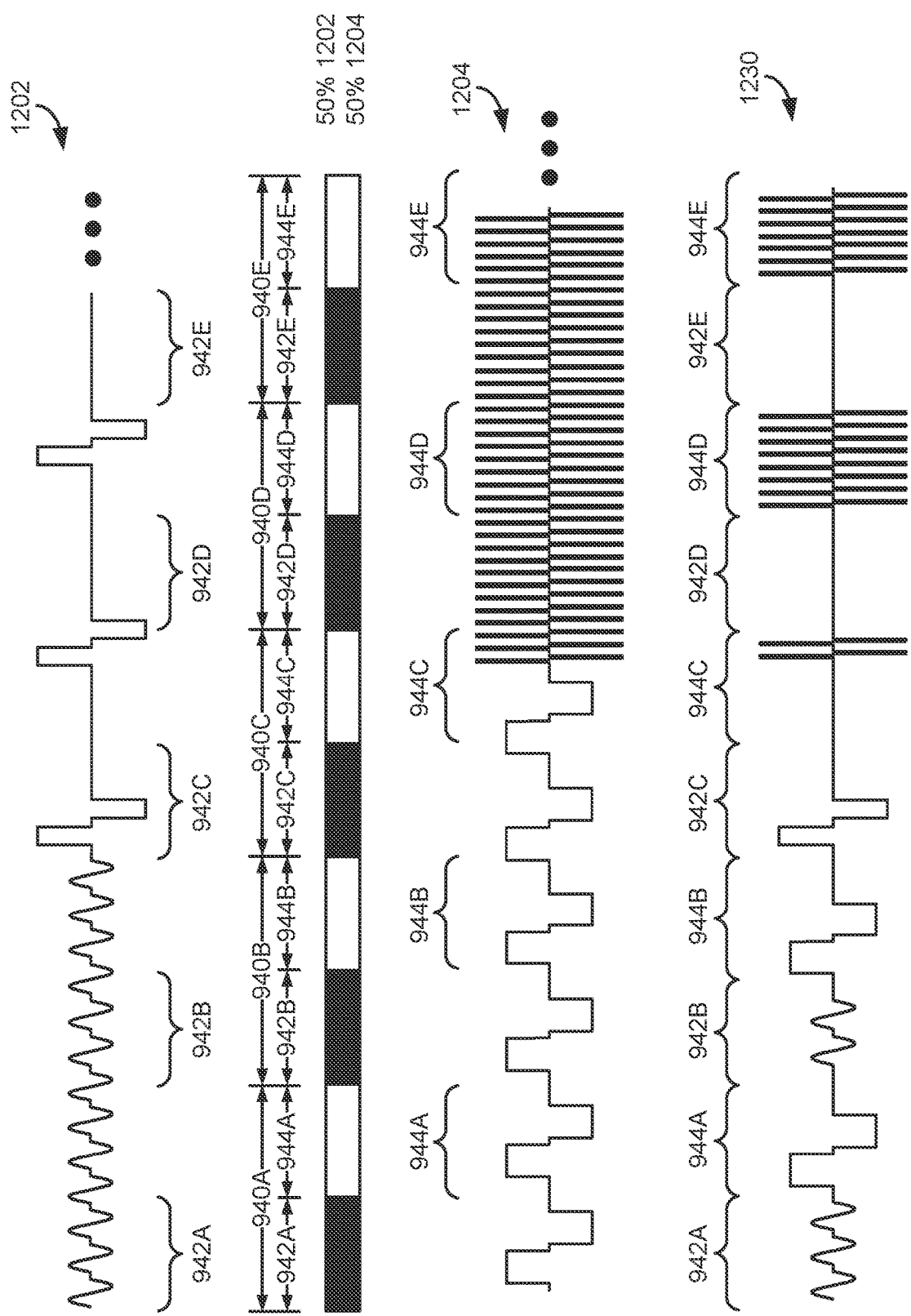
FIG. 13 illustrates an example waveform that is formed for a mask time domain allocation mode of operation for two stimulation programs in accordance with an example of this disclosure.

FIG. 13 shows an example of the stimulation programs 1202 and 1204 as interleaved in accordance with a mask mode of operation using the epoch technique. In the mask mode of operation, the position within a stimulation program is not bookmarked at the end of each time period. Rather, the mask mode of operation specifies that the stimulation programs are to be continuously running (even during the time period in which another stimulation program is being executed and either actually running in the IPG's hardware or only in software) and that the control signals are to be provided to the stimulation circuitry only during each of the stimulation programs' time allocations. In the example shown, the input 702 specifies a time domain allocation of 50% for stimulation program 1202 and 50% for stimulation program 1204, and the selector 700 passes the control signals corresponding to stimulation program 1202 during time periods 942 and the control signals corresponding to stimulation program 1204 during time periods 944. As can be seen in the resulting waveform 1230 (which is shown for only one polarity), the portions of a particular stimulation program that occur during another stimulation program's associated time periods are simply skipped over. In the illustrated example, the selector 700 negotiates switching such that stimulation begins with the first new pulse within a stimulation program's associated time period and a pulse is only initiated if it can be completed within the time period. Thus, if a switch occurs when the switched-to stimulation program specifies an active pulse, no stimulation is delivered until the start of the subsequent pulse and only pulses that can be completed within a stimulation program's associated time period are initiated. As will be understood, switching between programs could alternatively be negotiated in different ways such as those described above.

While the waveforms defined by stimulation programs 1202 and 1204 are shown as examples of complex waveforms, it will be understood that different types of complex waveforms can be interleaved using the disclosed techniques. Other types of complex waveforms may include parameters that are modulated over time from pulse-to-pulse. For example, amplitude modulated, frequency modulated, and pulse width modulated waveforms are some examples of the types of complex waveforms that might be interleaved using the disclosed techniques. These types of complex waveforms are described in U.S. Pat. No. 9,700,725, which is incorporated herein by reference in its entirety.

While the examples in FIGS. 8-13 have shown the consistent ordering of stimulation programs within an epoch (i.e., the first time period is dedicated to the first stimulation program in each epoch, the second time period is dedicated to the second stimulation program in each epoch, etc.), such consistent ordering is not required. In another embodiment, the ordering may be random within each epoch (e.g., a first epoch allocates time to a first stimulation program, then a second stimulation program, and then a third stimulation program and a subsequent epoch allocates time to the second stimulation program, then the third stimulation program, and then the first stimulation program). In each embodiment, though, the allocation of time for each stimulation program within an epoch is determined based on the allocation defined by the input 702. Similarly, while the examples have shown epochs of equal length, this is also not necessary. In another embodiment, the length of each epoch may be determined randomly or may be selected randomly from a range of possible epoch durations. In yet another embodiment, epochs may not be used at all. In this free-running mode of operation, the selector 700 may simply pass control signals for selected stimulation programs to the DAC circuitry 72 in a way that maintains each selected stimulation program within a range of the allocation defined by the input 702. For example, the selector 700 may pass control signals for a first stimulation program until further execution of the first stimulation program would be outside of an acceptable range around its configured allocation, and the selector 700 may then pass control signals for a second stimulation program until further execution of the second stimulation program would be outside of an acceptable range around its configured allocation, at which point the selector 700 may switch back to the first stimulation program.

While interleaving has thus far been described in terms of interleaving stimulation programs as they are configured, in one embodiment, the configured stimulation programs may be modified when selected for interleaving. Specifically, the amplitude of stimulation that is provided by the selected stimulation programs may be normalized to avoid sudden and potentially uncomfortable changes in amplitude as the stimulation switches back and forth between the selected stimulation programs. Stimulation amplitude can be normalized according to different values such as the patient's perception threshold, discomfort threshold, evoked compound action potential (ECAP) threshold, or scaled value.

FIGS. 14A-14C illustrate different example graphical user interfaces that enable a user to provide the input 702 that specifies a time domain allocation between two of two or more configured stimulation programs. FIG. 14A shows a slider bar 1402 that enables a user to select the time domain allocation between a first stimulation program (P1) that is represented by a first endpoint of the slider bar 1402 and a second stimulation program (P2) that is represented by a second endpoint of the slider bar 1404 that is opposite the first endpoint. The time domain allocation between the first and second stimulation programs is set by positioning the slider 1404 at the appropriate location along the slider bar 1402. For example, when the slider 1404 is positioned at the first endpoint of the slider bar 1402, time is fully allocated to the first stimulation program (P1). Conversely, when the slider 1404 is positioned at the second endpoint of the slider bar 1402, time is fully allocated to the second stimulation program (P2). When the slider 1404 is positioned between the endpoints, the time domain allocation is based on the distance between the slider 1404 and each of the endpoints. For example, if the slider 1404 is positioned halfway between the endpoints, time is equally split between the first and second stimulation programs (i.e., 50% P1 and 50% P2). If the slider is positioned at a point that is 30% of the bar's total length away from the first endpoint, 70% of the time is allocated to the first stimulation program and 30% of the time is allocated to the second stimulation program.

FIG. 14B shows a slider bar 1406 that functions in a similar manner to the slider bar 1402 of FIG. 14A. The slider bar 1406 differs, though, in that a third stimulation program is represented by the midpoint of the slider bar 1406. In the illustrated example, a first stimulation program (P1) is represented by a first endpoint of the slider bar 1406, a second stimulation program (P2) is represented by a midpoint of the slider bar 1406, and a third stimulation program (P3) is represented by a second endpoint of the slider bar 1406 that is opposite the first endpoint. When the slider 1408 is positioned at any of these points (i.e., the first endpoint, the midpoint, or the second endpoint), time is fully allocated to the stimulation program that is represented by that point. When the slider 1408 is positioned between the first endpoint and the midpoint, time is allocated between the first stimulation program (P1) and the second stimulation program (P2) based on the distance between the slider 1408 and each of the first endpoint and the midpoint in the same manner as described above with respect to FIG. 14A. For example, when the slider 1408 is positioned halfway between the first endpoint and the midpoint, time is allocated equally between the first and second stimulation programs (50% P1 and 50% P2). Similarly, when the slider is positioned between the midpoint and the second endpoint, time is allocated between the second stimulation program (P2) and the third stimulation program (P3) based on the distance between the slider 1408 and each of the midpoint and the second endpoint. For example, when the slider 1408 is positioned halfway between the midpoint and the second endpoint, time is allocated equally between the second and third stimulation programs (50% P2 and 50% P3). While the slider bar 1406 enables time allocation between two of three configured stimulation programs, it will be understood that a different type of slider bar may accommodate additional stimulation programs such that the user may select a time domain allocation between the stimulation programs that are represented by any two neighboring points.

FIG. 14C shows a dial 1410 that functions in a similar manner to the slider bars 1402 and 1406. Rather than representing multiple stimulation programs at points along a line, however, the dial 1410 represents multiple stimulation programs at points along a circle. In the illustrated example, four stimulation programs (P1, P2, P3, and P4) are located at equal distances about the circle. As with the slider bars 1402 and 1406, when the slider 1412 is placed at any of these points, time is fully allocated to the stimulation program represented by that point. Likewise, when the slider 1412 is positioned between any two points, time is allocated between the stimulation programs that are represented by those two points according to the distance between the slider 1412 and each of the two points. Note that time can be allocated between the stimulation programs represented by any two neighboring points but not between the stimulation programs represented by two non-neighboring points (i.e., the points that represent P1 and P3 or P2 and P4). With each of the slider bars 1402 and 1406 and the dial 1410, the user may be able to select the stimulation program that is represented by each of the available points. For example, each point may include a selector that enables the user to select a stimulation program that is to be represented by the point from a list of configured stimulation programs.

FIGS. 15A and 15B illustrate different example graphical user interfaces that enable a user to provide the input 702 that specifies a time domain allocation between more than two configured stimulation programs. FIG. 15A shows a triangle interface 1502 that enables a user to select the time domain allocation between a first stimulation program (P1), a second stimulation program (P2), and a third stimulation program (P3) that are each represented by a different vertex of the triangle interface 1502. As with the slider bars and the dial, when the slider 1504 is positioned at any of these points (i.e., any vertex), time is fully allocated to the stimulation program that is represented by that point. When the slider 1504 is positioned along an edge of the triangle interface 1502, in one example, time can be allocated between the two stimulation programs that are represented by the vertices at the ends of the edge according to the distance between the slider 1504 and each of the vertices. For example, if the slider 1504 is positioned along the edge and halfway between the vertices that represent the first stimulation program (P1) and the second stimulation program (P2), time can be allocated equally between the first and second stimulation programs (50% P1 and 50% P2).

Alternatively, and regardless whether the slider 1504 is positioned within the interior of the triangle interface 1502 or at an edge, time can be allocated between the three stimulation programs that are represented by the different vertices according to the distance between the slider 1504 and each of the vertices. In one embodiment, time is allocated between the three stimulation programs as:

$$\% P_n = \frac{\frac{1}{d_{P_n}}}{\sum_{1}^{n} d_{P_n}} \times 100 \qquad \text{Eq. 1}$$

where $\% P_n$ is the percentage of time allocated to the nth stimulation program and $d_{P_n}$ is the distance between the slider 1504 and the vertex of the triangle interface 1502 that represents the nth stimulation program. The user can therefore control the allocation of time between stimulation programs by moving the slider 1504 closer to the vertices that represent desired stimulation programs. Although not shown, interface 1502 can also be rendered three dimensionally, with X, Y, and Z positions of the slider 1504 specifying the time allocation to be provided to each stimulation program.

FIG. 15B shows a hexagon interface 1506 that enables a user to select the time domain allocation between six different stimulation programs (P1-P6) that are each represented by a different vertex of the hexagon interface 1506. The hexagon interface 1506 functions in the same manner as the triangle interface 1502 except that it enables time to be allocated between six stimulation programs as opposed to three stimulation programs. For example, when the slider 1508 is positioned at any of the hexagon interface's vertices, time is fully allocated to the stimulation program that is represented by that vertex; when the slider 1508 is positioned along an edge, time can be allocated between the two stimulation programs that are represented by the vertices at the ends of the edge according to the distance between the slider 1508 and each of the vertices. And again, and regardless whether slider 1508 is positioned at an edge or within the interior of the hexagon interface 1506, time can be allocated between the six stimulation programs that are represented by the different vertices according to the distance between the slider 1508 and each of the vertices as set forth in Equation 1. Interface 1506 may also be alternatively rendered as a six-dimensional space, with positions of the slider 1508 along the six dimensions specifying the time allocation to be provided to each stimulation program.

As FIGS. 15A and 15B illustrate, different shape interfaces can be configured to enable the allocation of time between different numbers of stimulation programs. As will be appreciated, the shape of an interface can be selected to accommodate the desired number of stimulation programs. As with the slider bars 1402 and 1406 and the dial 1410, the user may be able to select the stimulation program that is represented by each of the available points for shape interfaces such as the triangle interface 1502, the hexagon interface 1506, or a similar interface that enables allocation of time between more than two stimulation programs.

Figure 16A:
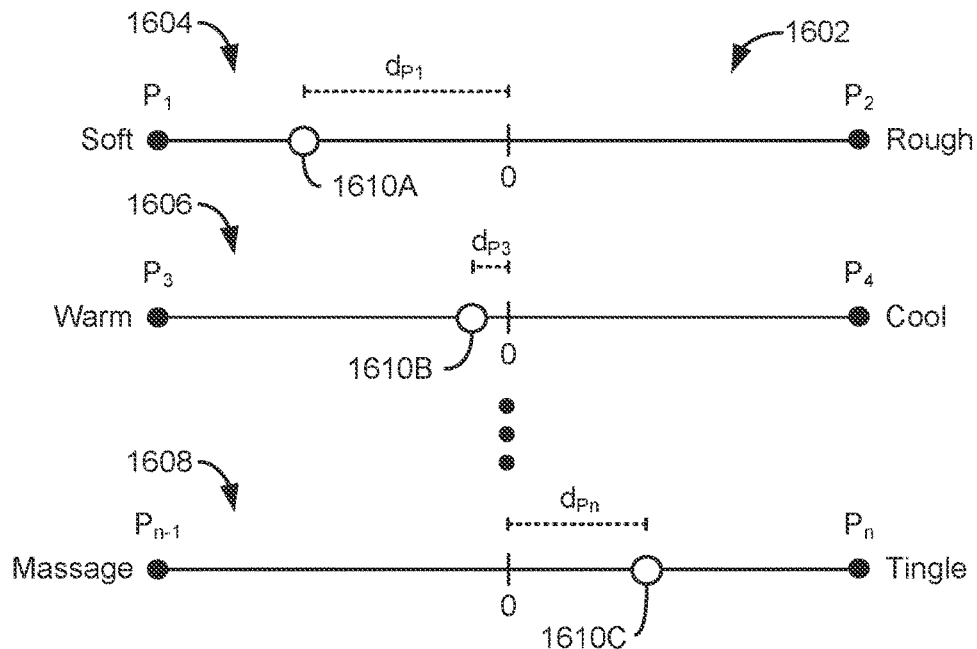
FIGS. 16A and 16B illustrate different equalizer-type graphical user interfaces for setting the time domain allocation between two or more stimulation programs in accordance with an example of this disclosure.
Figure 16B:
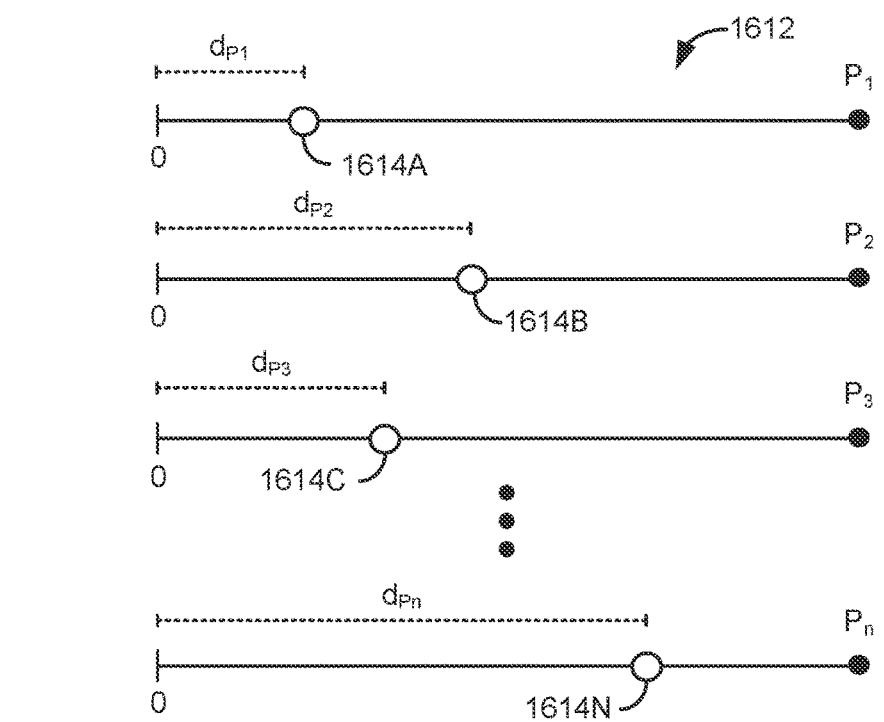

FIGS. 16A and 16B illustrate different example equalizer-type graphical user interfaces that enable a user to provide the input 702 that specifies a time domain allocation between multiple configured stimulation programs. FIG. 16A shows an equalizer interface 1602 that enables the user to allocate time between stimulation programs for different sensory dimensions. In the illustrated example, the sensory dimensions include a soft-rough dimension 1604, a warm-cool dimension 1606, and a massage-tingle dimension 1608. For each sensory dimension, a stimulation program, which may be user-selectable in the same manner as described above, is represented by each endpoint of an equalizer bar. For example, a first stimulation program (P1) is associated with a soft stimulation sensation and is represented by a first endpoint of the equalizer bar for the soft-rough sensory dimension 1604, and a second stimulation program (P2) is associated with a rough stimulation sensation and is represented by a second and opposite endpoint of the equalizer bar for the soft-rough sensory dimension 1604. When the slider 1610 is placed at an equalizer bar's midpoint, no time is allocated to either stimulation program for that particular sensory dimension. However, when the slider 1610 is moved away from the midpoint, an increasing portion of time is allocated to the stimulation program that is represented by the endpoint towards which the slider is moved. In the illustrated example, the user has selected stimulation that is soft, slightly warm, and tingly. In one embodiment, time is allocated between the stimulation programs for active sensory dimensions (i.e., sensory dimensions for which the associated slider is not positioned at the slider bar's midpoint) as:

$$\% P_n = \frac{d_{P_n}}{\sum_{1}^{n} d_{P_n}} \times 100 \qquad \text{Eq. 2}$$

where $\% P_n$ is the percentage of time allocated to the nth stimulation program and $d_{P_n}$ is the distance between the slider 1610 and the slider bar's midpoint for the nth stimulation program. The calculation is performed for the n selected stimulation programs (i.e., for the stimulation programs represented by a slider bar endpoint towards which the user moved the slider 1610 away from the midpoint). Using the equalizer interface 1602, the user can thus select between different sensations for different sensory dimensions that are represented by one or more equalizer bars.

FIG. 16B shows an equalizer interface 1612 that enables a user to allocate time between a number of stimulation programs. The interface 1612 functions in a similar manner to the interface 1602 except that each stimulation program is assigned to its own equalizer bar as opposed to two stimulation programs being represented by opposite ends of an equalizer bar. Using the interface, the user can independently allocate time between each of the stimulation programs by moving the sliders 1614 away from left endpoint of the equalizer bar towards the right endpoint of the equalizer bar. In one embodiment, time is allocated between the stimulation programs according to Equation 2, where $\% P_n$ is the percentage of time allocated to the nth stimulation program and $d_{P_n}$ is the distance between the slider 1614 and the slider bar's zero endpoint (e.g., the left endpoint in FIG. 16B). As with the interfaces described above, the user may be able to select the stimulation program that is represented by each of the available equalizer bars.

The interfaces described above may be presented on a display of the CP computer 202, the external controller 40, or another controller that is configured to communicate with an IPG 10 to enable a user to adjust the allocation of time between configured stimulation programs. The patient can use the interfaces to transition from a currently-active stimulation program to a different stimulation program or to interleave multiple configured stimulation programs in a manner that provides effective pain relief.

While the input to the selector 700 has so far been described as a manual entry (such as via one of the interfaces shown in FIGS. 14-16), in another embodiment, the user may select an automatic mode of operation according to which the input 702 is derived via an automatic adjustment algorithm to optimize the effectiveness of stimulation. In such an embodiment, the user may be periodically prompted to provide an indication of the effectiveness of the stimulation therapy that is currently being provided. For example, the user may be prompted to provide a numerical ranking of their pain level or a numerical ranking of their well-being. Based on the inputs provided by the user, the automatic adjustment algorithm then adjusts the settings (i.e., the time domain allocation of different stimulation programs) to move towards the settings that the patient has indicated provide the most effective therapy (i.e., tom optimize the indication of the effectiveness of the stimulation). Because the settings that constitute effective stimulation therapy may change over time, older user inputs may be given less weight than more recent user inputs.

In one particular example in which automatic adjustment may provide beneficial results, the user may configure a first stimulation program that provides sub-threshold stimulation and a second stimulation program that provides super-threshold stimulation. It is known that sub-threshold stimulation requires a wash-in period during which the sub-threshold stimulation is being delivered but does not provide optimal pain relief. In this type of arrangement, the automatic adjustment algorithm may allocate a small portion of time to the first stimulation program to facilitate the wash-in period and a larger portion of time to the second stimulation program, which may provide immediate relief. As the first stimulation program begins providing more effective pain relief (e.g., after the wash-in period), the user inputs would reflect a higher effectiveness and the automatic adjustment algorithm would increase the amount of time that is allocated to the first stimulation program and decrease the amount of time that is allocated to the second stimulation program. Thus, the user may simply select to employ the automatic mode of operation and allow the automatic adjustment algorithm to adjust the input 702. In the automatic mode of operation, one or more of the interfaces described above may be visible to the user, but the sliders may be adjusted according to the automatic adjustment algorithm and therefore not be adjustable by the user.

Although not illustrated, the interfaces described above may enable the user to specify additional settings associated with the allocation of time between stimulation programs. For example, the interfaces may allow the user to specify whether adjustments are made in a manual (i.e., the user adjusts the settings that ultimately provide the input 702) or automatic (i.e., the automatic adjustment algorithm adjusts the settings that ultimately provide the input 702) mode. The interfaces may additionally enable a user to specify whether epochs or free-running modes of operation are to be employed; the length of epochs; the order of time periods within an epoch (or random ordering), whether bookmark, mask, or re-initiate time domain allocation modes of operation are to be employed; and the settings that define the manner in which the selector 700 negotiates switching between stimulation programs (e.g., require pulse to be executable within time period, extend time period to complete active pulse, etc.).

Regardless of the particular settings, the input 702 is ultimately transmitted to the IPG 10 from the external device (i.e., output from the external device) on which adjustments are made (e.g., either manual or automatic adjustments), such as the CP computer 202 or the external controller 40, which causes the IPG 10 to interleave selected stimulation programs in time according to the specified time domain allocation. Although labeled as a single input 702 the input 702 may include a substantial amount of information. For example, the input 702 will specify the time domain allocation of each of multiple selected stimulation programs. In a preferred embodiment, the stimulation programs are stored on the IPG 10, and thus the input 702 may simply associate time domain allocations with identifiers of the corresponding stimulation programs. In another embodiment, if the stimulation programs are not stored on the IPG 10, the input 702 may specify the time domain allocation and the stimulation parameters for each stimulation program. The input 702 additionally specifies settings such as the duration of repeating epochs; the order of time periods within an epoch; whether bookmark, mask, or re-initiate modes of operation are to be employed; and the manner in which the selector 700 is to negotiate switching between stimulation programs.

Figure 17:
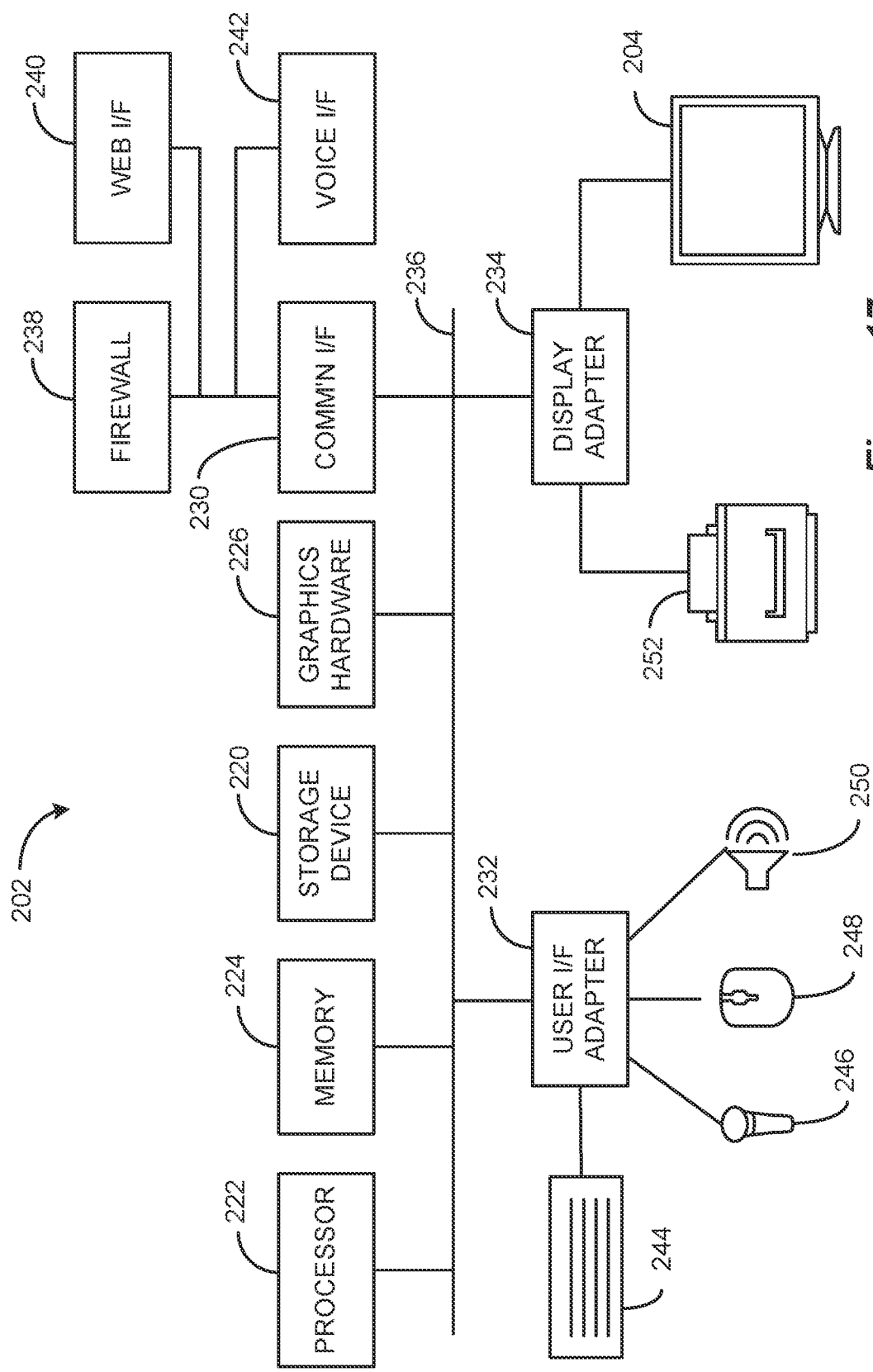
FIG. 17 illustrates a representative computing environment on which software that is associated with one or more aspects of the disclosure may be executed.

FIG. 17 illustrates the various components of an example CP computer 202 that may be configured to execute CP software 96. The CP computer 202 can include the processor 222, memory 224, storage 220, graphics hardware 226, communication interface 230, user interface adapter 232 and display adapter 234—all of which may be coupled via system bus or backplane 236. Memory 224 may include one or more different types of media (typically solid-state) used by the processor 222 and graphics hardware 226. For example, memory 224 may include memory cache, read-only memory (ROM), and/or random access memory (RAM). Storage 220 may store media, computer program instructions or software (e.g., CP software 96), preference information, device profile information, and any other suitable data. Storage 220 may include one or more non-transitory computer-readable storage mediums including, for example, magnetic disks (fixed, floppy, and removable) and tape, optical media such as CD-ROMs and digital versatile disks (DVDs), and semiconductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. As will be understood, the CP software 96 may be stored on a medium such as a CD or a USB drive, pre-loaded on a computing device such as the CP computer 202, or made available for download from a program repository via a network connection. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252. Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system. While the disclosed technique has been described primarily in the context of a CP computer 202, it will be understood that the techniques are equally applicable to other types of devices that might interface with an IPG 10 such as external controller 40 or general purposes devices that are configured for communication with the IPG 10. Such devices may include components similar to those illustrated in FIG. 17.

While the invention herein disclosed has been described by means of specific embodiments and applications thereof, numerous modifications and variations could be made thereto by those skilled in the art without departing from the scope of the invention set forth in the claims.

What is claimed is:

1. An external device comprising a display, and control circuitry that is configured to:
   present a graphical user interface on the display;
   receive via the graphical user interface a single input from a user;
   automatically determine a time domain allocation between a plurality of stimulation programs based on the single input;
   send stimulation parameters that define the plurality of stimulation programs to an implantable medical device, wherein each of the stimulation program defines at least one waveform to be formed at a set of electrodes that are connectable to the implantable medical device; and
   send an output that specifies the time domain allocation between the stimulation programs to the implantable medical device, wherein the output causes the implantable medical device to interleave the stimulation programs in time according to the time domain allocation.

2. The external device of claim 1, wherein single input is received at a slider of the graphical user interface.

3. The external device of claim 2, wherein the graphical user interface comprises a a representation of each of the stimulation programs, wherein the time domain allocation is set according to a position of the slider relative to the representations.

4. The external device of claim 3, wherein the graphical user interface comprises a shape with vertices, wherein the representation of one of the two or more stimulation programs occurs at each of the vertices.

5. The external device of claim 4, wherein the time domain allocation is set according to the position of the slider relative to each of the vertices.

6. The external device of claim 3, wherein the graphical user interface comprises a slider bar.

7. The external device of claim 6, wherein the slider bar comprises the representation of one of the stimulation programs at ends of the slider bar.

8. The external device of claim 1, wherein the control circuitry is further configured to receive an indication from a patient of an effectiveness of stimulation.

9. The external device of claim 8, wherein the control circuitry is configured to execute an algorithm to adjust the time domain allocation to optimize the indication of the effectiveness of stimulation.

10. The external device of claim 1, wherein at least one of the stimulation programs provides sub-threshold stimulation.

11. The external device of claim 10, wherein at least one of the stimulation programs provides super-threshold stimulation.

12. The external device of claim 1, wherein the output further specifies a duration of a repeating epoch.

13. The external device of claim 1, wherein the output further specifies a time domain allocation mode of operation.

14. The external device of claim 13, wherein the mode of operation specifies that each of the stimulation programs is to be re-initiated during each of its time allocations, or wherein the mode of operation specifies that a position should be stored at an end of each stimulation program's respective time allocation to mark a beginning position in a subsequent time allocation.

15. The external device of claim 13, wherein the mode of operation specifies that the stimulation programs are to be continuously running and that the control signals are to be provided to the stimulation circuitry only during each of the stimulation programs' time allocations.

16. The external device of claim 1, wherein the output specifies that the stimulation programs be executed in a single timing channel.

17. The external device of claim 1, wherein each of the stimulation programs is independently executable by the implantable medical device.

18. An external device comprising control circuitry that is configured to:
send stimulation parameters that define a plurality of stimulation programs to an implantable medical device, wherein each of the stimulation program defines at least one waveform to be formed at a set of electrodes that are connectable to the implantable medical device; and
send an output that specifies a time domain allocation between the stimulation programs to the implantable medical device, wherein the output causes the implantable medical device to interleave the stimulation programs in time according to the time domain allocation,
wherein the external device comprises a display, and wherein the control circuitry is further configured to present a graphical user interface on the display to enable a user to set the time domain allocation,
wherein the graphical user interface comprises one or more bars each comprising a slider, and a representation of each of the stimulation programs, wherein the time domain allocation is set according to a position of the one or more sliders relative to the representations.

19. The external device of claim 18, wherein each of the one or more bars comprises the representation of one of the stimulation programs at ends of each bar, wherein each of the one or more bars corresponds to a sensory dimension, and wherein the time domain allocation is set according to the positions of each slider relative to a midpoint of its associated bar.

20. The external device of claim 18, wherein the representation of only one of the stimulation programs is associated with each of the one or more bars.

* * * * *